United States Patent
Swayze

(10) Patent No.: US 10,493,092 B2
(45) Date of Patent: *Dec. 3, 2019

(54) ANTISENSE COMPOUNDS

(71) Applicant: Ionis Pharmaceuticals, Inc., Carlsbad, CA (US)

(72) Inventor: Eric E. Swayze, Encnitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 100 days.

This patent is subject to a terminal disclaimer.

(21) Appl. No.: 15/373,860

(22) Filed: Dec. 9, 2016

(65) Prior Publication Data

US 2017/0182082 A1    Jun. 29, 2017

Related U.S. Application Data

(63) Continuation of application No. 12/445,851, filed as application No. PCT/US2007/061850 on Oct. 18, 2007, now Pat. No. 9,550,988.

(60) Provisional application No. 60/852,894, filed on Oct. 18, 2006.

(51) Int. Cl.
| | | |
|---|---|---|
| *C07H 21/04* | (2006.01) | |
| *A61K 31/712* | (2006.01) | |
| *C12N 15/11* | (2006.01) | |
| *C12N 15/113* | (2010.01) | |
| *A61K 31/7125* | (2006.01) | |

(52) U.S. Cl.
CPC ........ *A61K 31/712* (2013.01); *A61K 31/7125* (2013.01); *C12N 15/111* (2013.01); *C12N 15/113* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/346* (2013.01); *C12N 2310/351* (2013.01); *C12N 2320/53* (2013.01)

(58) Field of Classification Search
None
See application file for complete search history.

(56) References Cited

PUBLICATIONS

Lima et al., "The positional influence of the helical geometry of the heteroduplex substrate on human RNase H1 catalysis" Molecular Pharmacology Fast Forward Published on Oct. 6, 2006 p. 1-47; Journal Publication: Molecular Pharmacology Jan. 2007, 71(1): 73-82.

*Primary Examiner* — Jennifer Pitrak McDonald
(74) *Attorney, Agent, or Firm* — McNeil Baur PLLC

(57) ABSTRACT

Provided herein are gapmer oligomeric compounds for reduction of target RNA in vivo comprising different nucleotide modifications within one or both wing regions. Also provided are methods of using such oligomeric compounds, including use in animals. In certain embodiments, such compound have desirable potency and toxicity characteristics.

31 Claims, No Drawings
Specification includes a Sequence Listing.

SEQUENCE LISTING

```
<160> NUMBER OF SEQ ID NOS: 11

<210> SEQ ID NO 1
<211> LENGTH: 19
<212> TYPE: DNA
<213> ORGANISM: Artificial Sequence
<220> FEATURE:
<223> OTHER INFORMATION: PCR Primer

<400> SEQUENCE: 1
gccacaggct cccagacat                                                 19

<210> SEQ ID NO 2
<211> LENGTH: 25
<212> TYPE: DNA
<213> ORGANISM: Artificial Sequence
<220> FEATURE:
<223> OTHER INFORMATION: PCR Primer

<400> SEQUENCE: 2
tccatcctct tgatatctcc ttttg                                          25

<210> SEQ ID NO 3
<211> LENGTH: 31
<212> TYPE: DNA
<213> ORGANISM: Artificial Sequence
<220> FEATURE:
<223> OTHER INFORMATION: PCR Probe

<400> SEQUENCE: 3
acagccatca tcaaagagat cgttagcaga a                                   31

<210> SEQ ID NO 4
<211> LENGTH: 24
<212> TYPE: DNA
<213> ORGANISM: Artificial Sequence
<220> FEATURE:
<223> OTHER INFORMATION: PCR Primer

<400> SEQUENCE: 4
atgacaatca tgttgcagca attc                                           24

<210> SEQ ID NO 5
<211> LENGTH: 25
<212> TYPE: DNA
<213> ORGANISM: Artificial Sequence
```

```
<220> FEATURE:
<223> OTHER INFORMATION: PCR Primer

<400> SEQUENCE: 5
cgatgcaata aatatgcaca aatca                                          25

<210> SEQ ID NO 6
<211> LENGTH: 28
<212> TYPE: DNA
<213> ORGANISM: Artificial Sequence
<220> FEATURE:
<223> OTHER INFORMATION: PCR Probe

<400> SEQUENCE: 6
ctgtaaagct ggaaagggac ggactggt                                       28

<210> SEQ ID NO 7
<211> LENGTH: 2160
<212> TYPE: DNA
<213> ORGANISM: Mus musculus

<400> SEQUENCE: 7
ggcgccctgc tctcccggcg gggcggcgga gggggcgggc tggccggcgc acggtgatgt    60
ggcgggactc tttgtgcact gcggcaggat acgcgcttgg gcgtcgggac gcggctgcgc   120
tcagctctct cctctcggaa gctgcagcca tgatggaagt ttgagagttg agccgctgtg   180
aggccaggcc cggcgcaggc gagggagatg agagacggcg gcggccacgg cccagagccc   240
ctctcagcgc ctgtgagcag ccgcgggggc agcgccctcg gggagccggc cgggcggcgg   300
cggcggcagc ggcggcgggc ctcgcctcct cgtcgtctgt tctaaccggg cagcttctga   360
gcagcttcgg agagagacgg tggaagaagc cgtgggctcg agcgggagcc ggcgcaggct   420
cggcggctgc acctcccgct cctggagcgg ggggagaag cggcggcggc ggccgcggct    480
ccggggaggg ggtcggagtc gcctgtcacc attgccaggg ctgggaacgc ggagagttg    540 ctctctcccc ttctcctgcc tccaacacgg cggcggcggc ggcggcacgt ccagggaccc   600
gggccggtgt taagcctccc gtccgccgcc gccgcacccc ccctggcccg ggctccggag   660
gccgccggag gaggcagccg ctgcgaggat tatccgtctt ctccccattc cgctgcctcg    720
gctgccaggc ctctggctgc tgaggagaag caggcccagt ctctgcaacc atccagcagc   780
cgccgcagca gccattaccc ggctgcggtc cagggcaag cggcagcaga gcgaggggca    840
tcagcgaccg ccaagtccag agccatttcc atcctgcaga agaagcctcg ccaccagcag   900
cttctgccat ctctctcctc cttttcttc agccacaggc tcccagacat gacagccatc    960
atcaaagaga tcgttagcag aaacaaaagg agatatcaag aggatggatt cgacttagac  1020
ttgacctata tttatccaaa tattattgct atgggatttc ctgcagaaag acttgaaggt  1080
gtatacagga acaatattga tgatgtagta aggttttggg attcaaagca taaaaaccat  1140
tacaagatat acaatctatg tgctgagaga cattatgaca ccgccaaatt taactgcaga  1200
gttgcacagt atcctttga agaccataac ccaccacagc tagaacttat caaacccttc   1260
tgtgaagatc ttgaccaatg gctaagtgaa gatgacaatc atgttgcagc aattcactgt  1320
aaagctggaa agggacggac tggtgtaatg atttgtgcat atttattgca tcggggcaaa  1380
tttttaaagg cacaagaggc cctagatttt tatggggaag taaggaccag agacaaaaag  1440
ggagtcacaa ttcccagtca gaggcgctat gtatattatt atagctacct gctaaaaaat  1500
cacctggatt acagacccgt ggcactgctg tttcacaaga tgatgtttga aactattcca  1560
```

```
atgttcagtg gcggaacttg caatcctcag tttgtggtct gccagctaaa ggtgaagata    1620
tattcctcca attcaggacc cacgcggcgg gaggacaagt tcatgtactt tgagttccct    1680
cagccattgc ctgtgtgtgg tgatatcaaa gtagagttct tccacaaaca gaacaagatg    1740
ctcaaaaagg acaaaatgtt tcacttttgg gtaaatacgt tcttcatacc aggaccagag    1800
gaaacctcag aaaaagtgga aaatggaagt ctttgtgatc aggaaatcga tagcatttgc    1860
agtatagagc gtgcagataa tgacaaggag tatcttgtac tcaccctaac aaaaaacgat    1920
cttgacaaag caaacaaaga caaggccaac cgatacttct ctccaaattt taaggtgaaa    1980
ctatacttta caaaaacagt agaggagcca tcaaatccag aggctagcag ttcaacttct    2040
gtgactccag atgttagtga caatgaacct gatcattata gatattctga caccactgac    2100
tctgatccag agaatgaacc ttttgatgaa gatcagcatt cacaaattac aaaagtctga    2160

<210> SEQ ID NO 8
<211> LENGTH: 14
<212> TYPE: DNA
<213> ORGANISM: Artificial Sequence
<220> FEATURE:
<223> OTHER INFORMATION: Antisense Compound

<400> SEQUENCE: 8
tcatggctgc agct                                                       14

<210> SEQ ID NO 9
<211> LENGTH: 15
<212> TYPE: DNA
<213> ORGANISM: Artificial Sequence
<220> FEATURE:
<223> OTHER INFORMATION: Antisense Compound

<400> SEQUENCE: 9
cggtacatgg aagtc                                                      15

<210> SEQ ID NO 10
<211> LENGTH: 18
<212> TYPE: DNA
<213> ORGANISM: Artificial Sequence
<220> FEATURE:
<223> OTHER INFORMATION: Antisense Compound

<400> SEQUENCE: 10
ctgctagcct ctggattt                                                   18

<210> SEQ ID NO 11
<211> LENGTH: 12
<212> TYPE: DNA
<213> ORGANISM: Artificial Sequence
<220> FEATURE:
<223> OTHER INFORMATION: Antisense Compound

<400> SEQUENCE: 11
tggtccagag cc                                                         12
```

ANTISENSE COMPOUNDS

SEQUENCE LISTING

The present application is being filed along with a Sequence Listing in electronic format. The Sequence Listing is provided as a file entitled CORE0070USC1SEQ_ST25.txt, created on Dec. 8, 2016, which is 8 Kb in size. The information in the electronic format of the sequence listing is incorporated herein by reference in its entirety.

BACKGROUND

Targeting disease-causing gene sequences was first suggested nearly 40 years ago (Belikova et al., Tet. Lett., 1967, 37, 3557-3562), and antisense activity was demonstrated in cell culture a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate expression of specific disease-causing genes. Another advantage is that validation of a target using antisense compounds results in direct and immediate discovery of the therapeutic agent.

Generally, the principle behind antisense technology is that an antisense compound hybridizes to a target nucleic acid and effects modulation of gene expression activity or function, such as transcription, translation or splicing. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi is a form of antisense-mediated gene silencing involving the introduction of dsRNA leading to the sequence-specific reduction of targeted endogenous mRNA levels. This sequence-specificity makes antisense compounds extremely attractive as tools for target validation and gene functionalization, as well as therapeutics to selectively modulate the expression of genes involved in the pathogenesis of any one of a variety of diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA.

Despite the expansion of knowledge since the discovery of antisense technology, there remains an unmet need for antisense compounds with greater efficacy, reduced toxicity and lower cost. The high-affinity methyleneoxy (4'-$CH_2$—O-2') bicyclic nucleic acid (BNA) moiety, also know as "Locked Nucleic Acid" (LNA) moiety, has been used to create potent gapmer antisense oligonucleotides. It has been shown, however, that this potency is accompanied by an increased risk of hepatotoxicity as indicated by elevation of liver transaminases in rodent experiments. Thus, provided herein are gapmer antisense compounds for inhibition of target RNA in vivo comprising high-affinity bicyclic nucleotide modifications, but which are designed to have mitigated toxicity by incorporation of non-bicyclic high-affinity modified nucleotides. Such gapmer antisense compounds are more effective than previously described BNA or LNA antisense compounds, as a result of a reduction in toxicity.

SUMMARY

Disclosed herein are gapmer antisense oligonucleotides which exhibit marked improvements in safety as compared to a gapmer of the same length and wing-gap-wing configuration, wherein each wing nucleotide is a bicyclic nucleic acid (BNA), for example a methyleneoxy (4'-$CH_2$—O-2') BNA, sometimes also referred to as LNA. The gapmer antisense oligonucleotides of the present invention comprise a deoxy gap region, a 5' wing region positioned at the 5' end of the deoxy gap, and a 3' wing region positioned at the 3' end of the deoxy gap, wherein at least one nucleotide of at least one of the wing regions is a 4' to 2' bicyclic nucleotide and at least one of the remaining wing nucleotides is a non-bicyclic high-affinity modified nucleotide. In an aspect of the invention, the non-bicyclic high-affinity modified nucleotides are non-bicyclic 2'-modified nucleotides. In certain embodiments, the gapmer antisense oligonucleotides have at least one LNA nucleotide (methyleneoxy (4'-$CH_2$—O-2') BNA) or ethyleneoxy (4'-$CH_2CH_2$—O-2') BNA in at least one of the wings and at least one non-bicyclic high-affinity modified nucleotide. The non-bicyclic 2'-modified nucleosides can be substituted at the 2'-position with substituted or unsubstituted —O-alkyl or substituted or unsubstituted —O-(2-acetylamide). For example, the non-bicyclic 2'-modified nucleosides could be 2'-$OCH_3$, 2'-$O(CH_2)_2OCH_3$, or 2'-$OCH_2C(O)$—$NR_1R_2$, wherein $R_1$ and $R_2$ are independently hydrogen or substituted or unsubstituted alkyl or, in the alternative, are taken together to make a heterocyclic moiety.

In addition, disclosed herein are gapmer antisense oligonucleotides having a deoxy gap, a 5' wing region positioned at the 5' end of the deoxy gap, and a 3' wing region positioned at the 3' end of the deoxy gap, wherein the 5' wing region has at least one non-bicyclic high-affinity modified nucleotide and the 3' wing region has at least one 4' to 2' bicyclic nucleotide, for example a LNA nucleotide (methyleneoxy (4'-$CH_2$—O-2') BNA) or an ethyleneoxy (4'-$CH_2CH_2$—O-2') BNA. In an exemplary aspect of the invention, the non-bicyclic high-affinity modified nucleotides are non-bicyclic 2'-modified nucleosides. In an additional embodiment of the present invention are gapmer antisense oligonucleotides, wherein the non-bicyclic 2'-modified nucleosides are substituted at the 2' position, for example 2'-$OCH_3$, 2'-$O(CH_2)_2OCH_3$, or 2'-$OCH_2C(O)$—$NR_1R_2$, wherein $R_1$ and $R_2$ are independently hydrogen or substituted or unsubstituted alkyl or, in the alternative, are taken together to make a heterocyclic moiety.

In a certain embodiment, the gapmer antisense oligonucleotides have no BNAs in the 5' wing region, for example no LNA nucleosides (methyleneoxy (4'-$CH_2$—O-2') BNAs) or ethyleneoxy (4'-$CH_2CH_2$—O-2') BNAs. In an additional embodiment, the gapmer antisense oligonucleotides disclosed herein have a 5' wing region having only 2'-$O(CH_2)_2$ $OCH_3$ modified nucleotides and only LNA nucleosides (methyleneoxy (4'-$CH_2$—O-2') BNAs) or ethyleneoxy (4'-$CH_2CH_2$—O-2') BNAs in the 3' wing.

In yet another embodiment, the gapmer antisense oligonucleotides, wherein the 5' region has at least one 4' to 2' bicyclic nucleotide and the 3' wing region has at least one non-bicyclic 2'-modified nucleotide. In a certain embodiment, the gapmer antisense oligonucleotides have no LNA nucleotides in the 3' wing region, for example no LNA nucleotides (methyleneoxy (4'-$CH_2$—O-2') BNAs) or ethyleneoxy (4'-CH$_2$CH$_2$—O-2') BNAs. In an additional embodiment, the gapmer antisense oligonucleotides disclosed herein have a 5' wing region having only BNA nucleotides, for example only LNA nucleotides (methyleneoxy (4'-CH$_2$—O-2') BNAs) or ethyleneoxy (4'-CH$_2$CH$_2$—O-2') BNAs, and a 3' wing region having only 2'-modified nucleosides, for example the non-bicyclic 2'-modified nucleosides can be substituted at the 2'-position with substituted or unsubstituted —O-alkyl or substituted or unsubstituted —O-(2-acetylamide). For example, the non-bicyclic 2'-modified nucleosides could be 2'-OCH$_3$, 2'-O(CH$_2$)$_2$OCH$_3$, or 2'-OCH$_2$C(O)—NR$_1$R$_2$, wherein R$_1$ and R$_2$ are independently hydrogen or substituted or unsubstituted alkyl or, in the alternative, are taken together to make a heterocyclic moiety.

The gapmer antisense oligonucleotides of the present invention can be shortmers or gap-widened antisense oligonucleotides. In certain embodiments, the gapmer antisense oligonucleotides are 10 to 30, 10 to 14, 12 to 25, 15 to 25, or 18 to 24 nucleotides in length. The 5' and 3' wing regions of the antisense compounds of the present invention are independently between 1 and 7 nucleotides in length, or 1, 2, 3, 4, 5, 6 or 7 nucleotides in length; between 1 and 5 nucleotides in length, or 1, 2, 3, 4, or 5 nucleotides in length; or between 1 to 3 nucleotides in length, or 1, 2, or 3 nucleotides in length. The deoxy gap region of the antisense oligonucleotides of the present invention are between 6 and 18 nucleotides in length or 6, 7, 8, 9, 10, 11, 12, 13, 14, 15, 16, 17, or 18 nucleotides in length; between 8 and 16 nucleotides in length, or 8, 9, 10, 11, 12, 13, 14, 15, or 16 nucleotides in length; between about 11 and 16 nucleotides in length, or 11, 12, 13, 14, 15, or 16; or between 7 and 10 nucleotides in length, or 7, 8, 9, or 10 nucleotides in length. In one aspect of the invention the gapmer antisense oligonucleotides have a wing-gap-wing configuration of 5-10-5, 4-12-4, 3-14-3, 2-16-2, 1-18-1, 3-10-3, 2-10-2, 1-10-1 or 2-8-2.

The gapmer antisense oligonucleotides delineated herein have at least one modified internucleoside linkage. In a certain embodiment this modified internucleoside linkage is a phosphorothioate. In an additional embodiment each internucleoside linkage is a phosphorothioate modified internucleoside linkage Also contemplated herein, are methods of reducing the expression of a target RNA in an animal comprising administering to said animal a gapmer antisense oligonucleotide of the present invention, wherein the sequence of said gapmer antisense oligonucleotide is complementary to said target RNA.

In one embodiment, the high-affinity modified nucleotides are sugar-modified nucleotides. In one aspect, at least one of the sugar-modified nucleotides comprises a bridge between the 4' and the 2' position of the sugar. Each of the sugar-modified nucleotides is, independently, β-D or α-L. In another aspect, each of said high-affinity modified nucleotides confers a ΔT$_m$ of at least 1 to 4 degrees per nucleotide. In another aspect, each of said sugar-modified nucleotides comprises a 2'-substituent group that is other than H or OH. Such sugar-modified nucleotides include those having a 4' to 2' bridged bicyclic nucleotide. In another aspect, each of the sugar-modified nucleotides is a non-bicyclic 2'-substituent groups, which are independently, alkoxy, substituted alkoxy, substituted or unsubstituted —O-(2-acetylamide) or halogen. In one embodiment, each of the 2'-substituent groups is OCH$_2$CH$_2$OCH$_3$.

In one embodiment, the gapmer antisense compounds have one or more sugar-modified nucleotides comprising a bridge between the 4' and 2' position of the sugar, wherein each of said bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$— and —N(R$_1$)—;

wherein x is 0, 1, or 2;

n is 1, 2, 3, or 4;

each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In one aspect, each of said bridges is, independently, —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. In another aspect, each of said bridges is, independently, 4'-(CH$_2$)$_2$-2', 4'-(CH$_2$)$_2$-2', 4'-CH$_2$—O-2', 4'-(CH$_2$)$_2$—O-2', 4'-CH$_2$—O—N(R$_1$)-2' and 4'-CH$_2$—N(R$_1$)—O-2'- wherein each R$_1$ is, independently, H, a protecting group or C$_1$-C$_{12}$ alkyl.

In another aspect of the invention are gapmer antisense compounds with one or more 2'-modified or 2'-substituted nucleosides. The term "2'-modified nucleoside" or "2'-substituted nucleoside" as used in the present invention is intended to include all manner of nucleosides having a 2'-substituent group that is other than H and OH. Suitable 2'-substituent groups for 2'-modified nucleosides of the invention include, but are not limited to: halo, allyl, amino, azido, amino, SH, CN, OCN, CF$_3$, OCF$_3$, O-, S-, or N(R$_m$)-alkyl; O-, S-, or N(R$_m$)-alkenyl; O-, S- or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with substituent groups selected from hydroxyl, amino, alkoxy, carboxy, benzyl, phenyl, nitro (NO$_2$), thiol, thioalkoxy (S-alkyl), halogen, alkyl, aryl, alkenyl and alkynyl where each R$_m$ is, independently, H, an amino protecting group or substituted or unsubstituted C$_1$-C$_{10}$ alkyl.

A list of 2'-substituent groups includes F, —NH$_2$, N$_3$, OCF$_3$, O—CH$_3$, O(CH$_2$)$_3$NH$_2$, CH$_2$—CH=CH$_2$, —O—CH$_2$—CH=CH$_2$, OCH$_2$CH$_2$OCH$_3$, 2'-O(CH$_2$)$_2$SCH$_3$, O—(CH$_2$)$_2$—O—N(R$_m$)(R$_n$), —O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl. Another list of 2'-substituent groups includes F, OCF$_3$, O—CH$_3$, OCH$_2$CH$_2$OCH$_3$, 2'-O(CH$_2$)$_2$SCH$_3$, O—(CH$_2$)$_2$—O—N(R$_m$)(R$_n$), —O(CH$_2$)$_2$O(CH$_2$)$_2$N(CH$_3$)$_2$, and N-substituted acetamides (O—CH$_2$—C(=O)—N(R$_m$)

($R_n$) where each $R_m$ and $R_n$ is, independently, H, an amino protecting group or substituted or unsubstituted $C_1$-$C_{10}$ alkyl.

Provided herein are gapmer antisense compounds for use in therapy. Further provided is the use of a gapmer antisense compound of the present invention for inhibiting expression of a target RNA in an animal.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989; which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, the term "nucleoside" means a glycosylamine comprising a nucleobase and a sugar. Nucleosides includes, but are not limited to, natural nucleosides, abasic nucleosides, modified nucleosides, and nucleosides having mimetic bases and/or sugar groups.

As used herein, the term "natural nucleoside" or "unmodified nucleoside" means a nucleoside comprising a natural nucleobase and a natural sugar. Natural nucleosides include RNA and DNA nucleosides.

As used herein, the term "natural sugar" refers to a sugar of a nucleoside that is unmodified from its naturally occurring form in RNA (2'-OH) or DNA (2'-H).

As used herein, the term "nucleotide" refers to a nucleoside having a phosphate group covalently linked to the sugar. Nucleotides may be modified with any of a variety of substituents.

As used herein, the term "nucleobase" refers to the base portion of a nucleoside or nucleotide. A nucleobase may comprise any atom or group of atoms capable of hydrogen bonding to a base of another nucleic acid.

As used herein, the term "natural nucleobase" refers to a nucleobase that is unmodified from its naturally occurring form in RNA or DNA.

As used herein, the term "heterocyclic base moiety" refers to a nucleobase comprising a heterocycle.

As used herein, the term "oligomeric compound" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds comprise conjugate groups. Nonlimiting examples of oligomeric compounds include, but are not limited to, primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

As used herein "oligonucleoside" refers to an oligonucleotide in which the internucleoside linkages do not contain a phosphorus atom.

As used herein, the term "oligonucleotide" refers to an oligomeric compound comprising a plurality of linked nucleotides or nucleosides. In certain embodiment, one or more nucleotides of an oligonucleotide is modified. In certain embodiments, an oligonucleotide comprises ribonucleic acid (RNA) or deoxyribonucleic acid (DNA). In certain embodiments, oligonucleotides are composed of natural and/or modified nucleobases, sugars and covalent internucleoside linkages, and may further include non-nucleic acid conjugates.

As used herein "internucleoside linkage" refers to a covalent linkage between adjacent nucleosides.

As used herein "natural internucleotide linkage" refers to a 3' to 5' phosphodiester linkage.

As used herein, the term "modified internucleoside linkage" refers to any linkage between nucleosides or nucleotides other than a naturally occurring internucleoside linkage.

As used herein, the term "antisense compound" refers to an oligomeric compound that is at least partially complementary to a target nucleic acid molecule to which it hybridizes. In certain embodiments, an antisense compound modulates (increases or decreases) expression of a target nucleic acid. Antisense compounds include, but are not limited to, compounds that are oligonucleotides, oligonucleosides, oligonucleotide analogs, oligonucleotide mimetics, and chimeric combinations of these. Consequently, while all antisense compounds are oligomeric compounds, not all oligomeric compounds are antisense compounds.

As used herein, the term "antisense oligonucleotide" refers to an antisense compound that is an oligonucleotide.

As used herein, the term "antisense activity" refers to any detectable and/or measurable activity attributable to the hybridization of an antisense compound to its target nucleic acid. Such detection and or measuring may be direct or indirect. For example, in certain embodiments, antisense activity is assessed by detecting and or measuring the amount of target protein. In certain embodiments, antisense activity is assessed by detecting and/or measuring the amount of target nucleic acids and/or cleaved target nucleic acids and/or alternatively spliced target nucleic acids.

As used herein the term "detecting antisense activity" or "measuring antisense activity" means that a test for detecting or measuring antisense activity is performed on a sample and compared to that of a control sample. Such detection and/or measuring may include values of zero. Thus, if a test for detection of antisense activity results in a finding of no antisense activity (antisense activity of zero), the step of "detecting antisense activity" has nevertheless been performed.

As used herein the term "control sample" refers to a sample that has not been contacted with a test compound. In certain embodiments, a control sample is obtained prior to administration of an oligomeric compound to an animal. In certain embodiments, a control sample is obtained from an animal to which oligomeric compound is not administered. In certain embodiments, a reference standard is used as a surrogate for a control sample.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif. Any combination of modifications and or mimetic groups can comprise a chimeric oligomeric compound as described herein.

As used herein, the term "motif" refers to a pattern of unmodified and modified nucleotides or linkages in an oligomeric compound.

As used herein, the term "mixed-backbone antisense oligonucleotide" refers to an antisense oligonucleotide wherein at least one internucleoside linkage of the antisense oligonucleotide is different from at least one other internucleotide linkage of the antisense oligonucleotide.

As used herein, the term "target protein" refers to a protein, the modulation of which is desired.

As used herein, the term "target gene" refers to a gene encoding a target.

As used herein, the terms "target nucleic acid" refers to any nucleic acid molecule, the amount or function of which is capable of being modulated by an antisense compound. Target nucleic acids include, but are not limited to, RNA (including, but not limited to pre-mRNA and mRNA or portions thereof), cDNA derived from such RNA, as well as non-translated RNA, such as miRNA. For example, in certain embodiments, a target nucleic acid can be a cellular gene (or mRNA transcribed from such gene) whose expression is associated with a particular disorder or disease state, or a nucleic acid molecule from an infectious agent.

As used herein, the term "target region" refers to a portion of a target nucleic acid which, is capable of hybridizing one or more antisense compound and such hybridization results in antisense activity.

As used herein, the term "target segment" refers to a shorter sub-portions of a target region As used herein, the term "target site" refers to a portion of a target nucleic acid that is capable of hybridizing with an antisense compound, resulting in antisense activity.

As used herein, the term "targeting" or "targeted to" refers to the association of an antisense compound to a particular target nucleic acid molecule or a particular region of nucleotides within a target nucleic acid molecule.

As used herein, "designing" or "designed to" refer to the process of designing an oligomeric compound that specifically hybridizes with a selected target nucleic acid molecule.

As used herein, the term "nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

As used herein, the term "non-complementary nucleobase" refers to a pair of nucleobases that do not form hydrogen bonds with one another or otherwise support hybridization.

As used herein, the term "complementary" refers to the capacity of an oligomeric compound to hybridize to another oligomeric compound or nucleic acid through nucleobase complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% nucleobase complementary to a target nucleic acid.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, the term "specifically hybridizes" refers to the ability of an oligomeric compound to hybridize to one nucleic acid site with greater affinity than it hybridizes to another nucleic acid site. In certain embodiments, an antisense oligonucleotide specifically hybridizes to more than one target site. In certain embodiments, an oligomeric compound specifically hybridizes with its target under stringent hybridization conditions.

As used herein, the term "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

As used herein, the term "percent complementary" refers to the number of nucleobases of an oligomeric compound that have nucleobase complementarity with a corresponding nucleobase of another oligomeric compound or nucleic acid divided by the total length (number of nucleobases) of the oligomeric compound.

As used herein the term "region of percent complementarity" refers to the number of nucleobases of a region of an oligomeric compound that have nucleobase complementarity with a corresponding nucleobase of another oligomeric compound or nucleic acid divided by the total length (number of nucleobases) of the region.

As used herein, the term "modulation" refers to a perturbation of function or activity when compared to the level of the function or activity prior to modulation. For example, modulation includes the change, either an increase (stimulation or induction) or a decrease (inhibition or reduction) in gene expression. As further example, modulation of expression can include perturbing splice site selection of pre-mRNA processing.

As used herein, the term "expression" refers to all the functions and steps by which a gene's coded information is converted into structures present and operating in a cell. Such structures include, but are not limited to the products of transcription and translation.

As used herein, "variant" refers to an alternative RNA transcript that can be produced from the same genomic region of DNA. Variants include, but are not limited to "pre-mRNA variants" which are transcripts produced from the same genomic DNA that differ from other transcripts produced from the same genomic DNA in either their start or stop position and contain both intronic and exonic sequence. Variants also include, but are not limited to, those with alternate splice junctions, or alternate initiation and termination codons.

As used herein, the term "2'-modified" or "2'-substituted" means a sugar comprising substituent at the 2' position other than H or OH. 2'-modified monomers, include, but are not limited to, BNA's and monomers (e.g., nucleosides and nucleotides) with 2'-substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N($R_m$)($R_n$), or O—$CH_2$—C(=O)—N($R_m$)($R_n$), where each $R_m$ and $R_n$ is, independently, H or substituted or unsubstituted $C_1$-$C_{10}$ alkyl.

As used herein, the term "MOE" refers to a 2'-O-methoxyethyl substituent.

As used herein, the term "gapmer" refers to a chimeric oligomeric compound comprising a central region (a "gap") and a region on either side of the central region (the "wings"), wherein the gap comprises at least one modification difference compared to each wing. Such modifications include nucleobase, monomeric linkage, and sugar modifications as well as the absence of modification (unmodified RNA or DNA). Thus, in certain embodiments, the nucleotide linkages in each of the wings are different than the nucleotide linkages in the gap. In certain embodiments, each wing comprises nucleotides with high affinity modifications and the gap comprises nucleotides that do not comprise that modification. In certain embodiments the nucleotides in the gap and the nucleotides in the wings all comprise high affinity modifications, but the high affinity modifications in the gap are different than the high affinity modifications in each of the wings. In certain embodiments, the modifications in the wings are the same as one another. In certain embodiments, the modifications in the wings are different from each other. In certain embodiments, nucleotides in the gap are unmodified and nucleotides in the wings are modified. In certain embodiments, the modification(s) within each wing are the same. In certain embodiments, the modification(s) in one wing are different from the modification(s) in the other wing.

As used herein, the term "short antisense compound" or "shortmer oligonucleotide" refers to a gapmer antisense compound or antisense oligonucleotide 10, 11, 12, 13 or 14 nucleotides in length having a deoxy gap 6 to 12 nucleotides in length having wing regions that are independently 1 to 4 high-affinity modified nucleotides in length. Exemplary wing-deoxy gap-wing configurations are 4-6-4, 3-6-3, 2-6-2, 4-7-4, 3-7-3, 2-7-2, 4-8-4, 3-8-3, 2-8-2, 1-8-1, 2-9-2, 1-9-1, 2-10-2, 1-10-1, 1-12-1, and the like.

As used herein, a "gap-widened antisense oligonucleotide" refers to a chimeric antisense oligonucleotide with a deoxy gap region which is greater than 10 nucleotides in length having wing regions that are independently one to eight high-affinity modified nucleotides in length. In preferred embodiments, the gap-widened antisense oligonucleotides are 18 to 24 nucleotides in length capable of having, for example, various wing-gap-wing motifs selected from: 1-16-1, 2-15-1, 1-15-2, 1-14-3, 3-14-1, 2-14-2, 1-13-4, 4-13-1, 2-13-3, 3-13-2, 1-12-5, 5-12-1, 2-12-4, 4-12-2, 3-12-3, 1-11-6, 6-11-1, 2-11-5, 5-11-2, 3-11-4, 4-11-3, 1-17-1, 2-16-1, 1-16-2, 1-15-3, 3-15-1, 2-15-2, 1-14-4, 4-14-1, 2-14-3, 3-14-2, 1-13-5, 5-13-1, 2-13-4, 4-13-2, 3-13-3, 1-12-6, 6-12-1, 2-12-5, 5-12-2, 3-12-4, 4-12-3, 1-11-7, 7-11-1, 2-11-6, 6-11-2, 3-11-5, 5-11-3, 4-11-4, 1-18-1, 1-17-2, 2-17-1, 1-16-3, 1-16-3, 2-16-2, 1-15-4, 4-15-1, 2-15-3, 3-15-2, 1-14-5, 5-14-1, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 4-12-4, 1-11-8, 8-11-1, 2-11-7, 7-11-2, 3-11-6, 6-11-3, 4-11-5, 5-11-4, 1-18-1, 1-17-2, 2-17-1, 1-16-3, 3-16-1, 2-16-2, 1-15-4, 4-15-1, 2-15-3, 3-15-2, 1-14-5, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 4-12-4, 1-11-8, 8-11-1, 2-11-7, 7-11-2, 3-11-6, 6-11-3, 4-11-5, 5-11-4, 1-19-1, 1-18-2, 2-18-1, 1-17-3, 3-17-1, 2-17-2, 1-16-4, 4-16-1, 2-16-3, 3-16-2, 1-15-5, 2-15-4, 4-15-2, 3-15-3, 1-14-6, 6-14-1, 2-14-5, 5-14-2, 3-14-4, 4-14-3, 1-13-7, 7-13-1, 2-13-6, 6-13-2, 3-13-5, 5-13-3, 4-13-4, 1-12-8, 8-12-1, 2-12-7, 7-12-2, 3-12-6, 6-12-3, 4-12-5, 5-12-4, 2-11-8, 8-11-2, 3-11-7, 7-11-3, 4-11-6, 6-11-4, 5-11-5, 1-20-1, 1-19-2, 2-19-1, 1-18-3, 3-18-1, 2-18-2, 1-17-4, 4-17-1, 2-17-3, 3-17-2, 1-16-5, 2-16-4, 4-16-2, 3-16-3, 1-15-6, 6-15-1, 2-15-5, 5-15-2, 3-15-4, 4-15-3, 1-14-7, 7-14-1, 2-14-6, 6-14-2, 3-14-5, 5-14-3, 4-14-4, 1-13-8, 8-13-1, 2-13-7, 7-13-2, 3-13-6, 6-13-3, 4-13-5, 5-13-4, 2-12-8, 8-12-2, 3-12-7, 7-12-3, 4-12-6, 6-12-4, 5-12-5, 3-11-8, 8-11-3, 4-11-7, 7-11-4, 5-11-6, 6-11-5, 1-21-1, 1-20-2, 2-20-1, 1-20-3, 3-19-1, 2-19-2, 1-18-4, 4-18-1, 2-18-3, 3-18-2, 1-17-5, 2-17-4, 4-17-2, 3-17-3, 1-16-6, 6-16-1, 2-16-5, 5-16-2, 3-16-4, 4-16-3, 1-15-7, 7-15-1, 2-15-6, 6-15-2, 3-15-5, 5-15-3, 4-15-4, 1-14-8, 8-14-1, 2-14-7, 7-14-2, 3-14-6, 6-14-3, 4-14-5, 5-14-4, 2-13-8, 8-13-2, 3-13-7, 7-13-3, 4-13-6, 6-13-4, 5-13-5, 1-12-10, 10-12-1, 2-12-9, 9-12-2, 3-12-8, 8-12-3, 4-12-7, 7-12-4, 5-12-6, 6-12-5, 4-11-8, 8-11-4, 5-11-7, 7-11-5, 6-11-6, 1-22-1, 1-21-2, 2-21-1, 1-21-3, 3-20-1, 2-20-2, 1-19-4, 4-19-1, 2-19-3, 3-19-2, 1-18-5, 2-18-4, 4-18-2, 3-18-3, 1-17-6, 6-17-1, 2-17-5, 5-17-2, 3-17-4, 4-17-3, 1-16-7, 7-16-1, 2-16-6, 6-16-2, 3-16-5, 5-16-3, 4-16-4, 1-15-8, 8-15-1, 2-15-7, 7-15-2, 3-15-6, 6-15-3, 4-15-5, 5-15-4, 2-14-8, 8-14-2, 3-14-7, 7-14-3, 4-14-6, 6-14-4, 5-14-5, 3-13-8, 8-13-3, 4-13-7, 7-13-4, 5-13-6, 6-13-5, 4-12-8, 8-12-4, 5-12-7, 7-12-5, 6-12-6, 5-11-8, 8-11-5, 6-11-7, or 7-11-6. In a particular embodiment, the gap-widened antisense oligonucleotides of the present invention have a 2-16-2, 3-14-3, or 4-12-4 wing-gap-wing motif.

As used herein, the term "high-affinity modified nucleotide" refers to a nucleotide having at least one modified nucleobase, internucleoside linkage or sugar moiety, such that the modification increases the affinity of an antisense compound comprising the modified nucleotide to a target nucleic acid. High-affinity modifications include, but are not limited to, BNAs, LNAs and 2'-MOE.

As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein, the term "bicyclic nucleoside" or "BNA" refers to a nucleoside wherein the furanose portion of the nucleoside includes a bridge connecting two atoms on the furanose ring, thereby forming a bicyclic ring system. BNAs include, but are not limited to, α-L-LNA, β-D-LNA, ENA, Oxyamino BNA (2'-O—N(CH$_3$)—CH$_2$-4') and Aminooxy BNA (2'-N(CH$_3$)—O—CH$_2$-4').

As used herein, the term "4' to 2' bicyclic nucleoside" refers to a BNA wherein the bridge connecting two atoms of the furanose ring bridges the 4' carbon atom and the 2' carbon atom of the furanose ring, thereby forming a bicyclic ring system.

Representative structures of BNA's include but are not limited to:

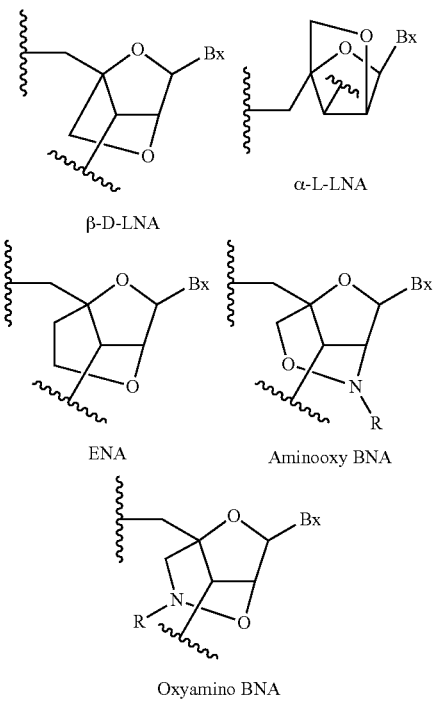

As used herein, a "locked nucleic acid" or "LNA" refers to a nucleotide modified such that the 2'-hydroxyl group of the ribosyl sugar ring is linked to the 4' carbon atom of the sugar ring via a methylene groups, thereby forming a 2'-C,4'-C-oxymethylene linkage. LNAs include, but are not limited to, α-L-LNA, and β-D-LNA.

As used herein, the term "prodrug" refers to a therapeutic agent that is prepared in an inactive form that is converted to an active form (i.e., drug) within the body or cells thereof by the action of endogenous enzymes or other chemicals and/or conditions.

As used herein, the term "pharmaceutically acceptable salts" refers to salts of active compounds that retain the desired biological activity of the active compound and do not impart undesired toxicological effects thereto.

As used herein, the term "cap structure" or "terminal cap moiety" refers to chemical modifications, which have been incorporated at either terminus of an antisense compound.

As used herein, the term "prevention" refers to delaying or forestalling the onset or development of a condition or disease for a period of time from hours to days, preferably weeks to months.

As used herein, the term "amelioration" refers to a lessening of at least one indicator of the severity of a condition or disease. The severity of indicators may be determined by subjective or objective measures which are known to those skilled in the art.

As used herein, the term "treatment" refers to administering a composition of the invention to effect an alteration or improvement of the disease or condition. Prevention, amelioration, and/or treatment may require administration of multiple doses at regular intervals, or prior to onset of the disease or condition to alter the course of the disease or condition. Moreover, a single agent may be used in a single individual for each prevention, amelioration, and treatment of a condition or disease sequentially, or concurrently.

As used herein, the term "pharmaceutical agent" refers to a substance provides a therapeutic benefit when administered to a subject.

As used herein, the term "therapeutically effective amount" refers to an amount of a pharmaceutical agent that provides a therapeutic benefit to an animal.

As used herein, "administering" means providing a pharmaceutical agent to an animal, and includes, but is not limited to administering by a medical professional and self-administering.

As used herein, the term "pharmaceutical composition" refers to a mixture of substances suitable for administering to an individual. For example, a pharmaceutical composition may comprise an antisense oligonucleotide and a sterile aqueous solution.

As used herein, the term "animal" refers to a human or non-human animal, including, but not limited to, mice, rats, rabbits, dogs, cats, pigs, and non-human primates, including, but not limited to, monkeys and chimpanzees.

As used herein, the term "parenteral administration," refers to administration through injection or infusion. Parenteral administration includes, but is not limited to, subcutaneous administration, intravenous administration, or intramuscular administration.

As used herein, the term "subcutaneous administration" refers to administration just below the skin. "Intravenous administration" means administration into a vein.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

As used herein, the term "dosage unit" refers to a form in which a pharmaceutical agent is provided. In certain embodiments, a dosage unit is a vial comprising lyophilized antisense oligonucleotide. In certain embodiments, a dosage unit is a vial comprising reconstituted antisense oligonucleotide.

As used herein, the term "active pharmaceutical ingredient" refers to the substance in a pharmaceutical composition that provides a desired effect.

As used herein, the term "side effects" refers to physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

As used herein, the term "therapeutic index" refers to some measure of activity or potency divided by some measure of toxicity.

As used herein, the term "alkyl," refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein, the term "alkenyl," refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, the term "alkynyl," refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, the term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

As used herein, the term "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

As used herein, the term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups.

As used herein, the term "alkoxy," refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

As used herein, the terms "halo" and "halogen," as used herein, refer to an atom selected from fluorine, chlorine, bromine and iodine.

As used herein, the terms "aryl" and "aromatic," refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substitutent groups.

As used herein, the terms "aralkyl" and "arylalkyl," refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substitutent groups attached to the alkyl, the aryl or both groups that form the radical group.

As used herein, the term "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups.

As used herein, the terms "heteroaryl," and "heteroaromatic," refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substitutent groups.

As used herein, the term "heteroarylalkyl," refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substitutent groups on one or both of the heteroaryl or alkyl portions.

As used herein, the term "mono or poly cyclic structure" includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

As used herein, the term "acyl," as used herein, refers to a radical formed by removal of a hydroxyl group from an organic acid an d has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substitutent groups.

As used herein, the term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

As used herein, the terms "substituent" and "substituent group," include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxo (—O—$R_{aa}$), aryl, aralkyl, heterocyclic, heteroaryl, heteroarylalkyl, amino (—$NR_{bb}R_{cc}$), imino (=$NR_{bb}$), amido (—C(O)$NR_{bb}R_{cc}$ or —N($R_{bb}$)C(O)$R_{aa}$), azido (—$N_3$), nitro (—$NO_2$), cyano (—CN), carbamido (—OC(O)$NR_{bb}R_{cc}$ or —N($R_{bb}$)C(O)O$R_{aa}$), ureido (—N($R_{bb}$)C(O)$NR_{bb}R_{cc}$), thioureido (—N($R_{bb}$)C(S)$NR_{bb}R_{cc}$), guanidinyl (—N($R_{bb}$)C(=$NR_{bb}$)$NR_{bb}R_{cc}$), amidinyl (—C(=$NR_{bb}$)$NR_{bb}R_{cc}$ or —N($R_{bb}$)C($NR_{bb}$)$R_{aa}$), thiol (—$SR_{bb}$), sulfinyl (—S(O)$R_{bb}$), sulfonyl (—S(O)$_2R_{bb}$), sulfonamidyl (—S(O)$_2NR_{bb}R_{cc}$ or —N($R_{bb}$)S(O)$_2R_{bb}$) and conjugate groups. Wherein each $R_{aa}$, $R_{bb}$ and $R_{cc}$ is, independently, H, an optionally linked chemical functional group or a further substitutent group with a preferred list including without limitation H, alkyl, alkenyl, alkynyl, aliphatic, alkoxy, acyl, aryl, aralkyl, heteroaryl, alicyclic, heterocyclic and heteroarylalkyl.

Overview

In certain embodiments, chemical modifications improve the potency and/or efficacy of antisense compounds, improving the potential for oral delivery as well as enhancing subcutaneous administration, decreasing the potential for side effects, and leading to improvements in patient convenience. In certain such embodiments, chemical modifications that increase the potency of antisense compounds allow administration of lower doses, which reduces the potential for toxicity, as well as decreasing overall cost of therapy. In certain embodiments, modifications that increase resistance to degradation result in slower clearance from the body, which in certain embodiments, allows for less frequent dosing.

In certain embodiments, oligomeric compounds comprising certain chemical modifications or motifs are less toxic than other oligomeric compounds comprising different modifications and/or motifs. In certain embodiments, administration of such oligomeric compounds results in less hepatotoxicity. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds. In certain embodiments, the invention provides oligomeric compounds that have favorable characteristics for in vivo administration.

To address the need for more potent antisense compounds with increased activity in vivo and less risk of hepatotoxicity, certain gapmer antisense compounds of the present invention have been designed. Certain gapmer antisense oligonucleotides of the present invention comprise a deoxy gap region, a 5' wing region positioned at the 5' end of the deoxy gap, and a 3' wing region positioned at the 3' end of the deoxy gap, wherein at least one nucleoside of at least one of the wing regions is a 4' to 2' bicyclic nucleoside and at least one of the remaining wing nucleosides is a non-bicyclic high-affinity modified nucleotide. High-affinity modified nucleotides include, but are not limited to, nucleotides with BNA, LNA or 2'-MOE modifications. Non-bicyclic high-affinity modified nucleotides include, but are not limited to, 2'-modified nucleotides. Certain such gapmer antisense compounds optionally can further comprise a conjugate group. Certain gapmer antisense compounds of the present invention are shortmers and/or gap-widened antisense oligonucleotides.

Certain Compounds

In certain embodiments, the present invention provides oligomeric compounds comprising oligonucleotides. Certain oligonuculeotides comprise 8 to 30 linked nucleosides. In certain embodiments, the olgomeric compounds comprise modified nucleosides, modified internucleoside linkages and/or conjugate groups.

The compounds described herein contain one or more asymmetric centers and thus give rise to enantiomers, diastereomers, and other stereoisomeric configurations that may be defined, in terms of absolute stereochemistry, as (R) or (S), a or B, or as (D) or (L) such as for amino acids et al. Included in the antisense compounds provided herein are all such possible isomers, as well as their racemic and optically pure forms.

Certain Nucleosides

In certain embodiments, the invention provides oligomeric compounds comprising linked nucleosides. In certain embodiments, some or all of the nucleosides are modified nucleosides. In certain embodiments, one or more nucleoside comprises a modified nucleobase. In certain embodiments, one or more nucleoside comprises a modified sugar.

In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. The terms modified nucleobase and nucleobase mimetic can overlap but generally a modified nucleobase refers to a nucleobase that is fairly similar in structure to the parent nucleobase, such as for example a 7-deaza purine, a 5-methyl cytosine, or a G-clamp, whereas a nucleobase mimetic would include more complicated structures, such as for example a tricyclic phenoxazine nucleobase mimetic. Methods for preparation of the above noted modified nucleobases are well known to those skilled in the art.

In certain embodiments, oligomeric compounds provided herein comprise one or more nucleosides having a modified sugar moiety. In certain embodiments, the furanosyl sugar ring of a natural nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C($R_1$)($R_2$) for the ring oxygen at the 4'-position. Modified sugar moieties are well known and can be used to alter, typically increase, the affinity of the antisense compound for its target and/or increase nuclease resistance. A representative list of modified sugars includes but is not limited to non-bicyclic substituted sugars, especially non-bicyclic 2'-substituted sugars having a 2'-F, 2'-OCH$_3$ or a 2'-O(CH$_2$)$_2$—OCH$_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and 6,600,032; and WO 2005/121371.

In certain embodiments, nucleosides comprise bicyclic modified sugars (BNA's), including LNA (4'-(CH$_2$)—O-2' bridge), 2'-thio-LNA (4'-(CH$_2$)—S-2' bridge), 2'-amino-LNA (4'-(CH$_2$)—NR-2' bridge), ENA (4'-(CH$_2$)$_2$—O-2' bridge), 4'-(CH$_2$)$_3$-2' bridged BNA, 4'-(CH$_2$CH(CH$_3$))-2' bridged BNA, cEt (4'-(CH(CH$_3$)—O-2' bridge), and cMOE BNAs (4'-(CH(CH$_2$OCH$_3$)—O-2' bridge). Certain such BNA's have been prepared and disclosed in the patent literature as well as in scientific literature (See, e.g., Srivastava, et al. J. Am. Chem. Soc. 2007, ACS Advanced online publication, 10.1021/ja071106y, Albaek et al. J. Org. Chem., 2006, 71, 7731-7740, Fluiter, et al. Chembiochem 2005, 6, 1104-1109, Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; WO 94/14226; WO 2005/021570; Singh et al., J. Org. Chem., 1998, 63, 10035-10039, WO 2007/090071; Examples of issued US patents and published applications that disclose BNAs include, for example, U.S. Pat. Nos. 7,053,207; 6,268,490; 6,770,748; 6,794,499; 7,034,133; and 6,525,191; and U.S. Pre-Grant Publication Nos. 2004-0171570; 2004-0219565; 2004-0014959; 2003-0207841; 2004-0143114; and 20030082807.

Also provided herein are "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—CH$_2$—) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., *Bioorganic Medicinal Chemistry*, 2003, 11, 2211-2226). LNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (Wahlestedt et al., *Proc. Natl. Acad. Sci. U.S.A.*, 2000, 97, 5633-5638).

An isomer of LNA that has also been studied is alpha-L-LNA which has been shown to have superior stability against a 3'-exonuclease. The alpha-L-LNA's were incorporated into antisense gapmers and chimeras that showed potent antisense activity (Frieden et al., *Nucleic Acids Research*, 2003, 21, 6365-6372).

The synthesis and preparation of the LNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Certain Internucleoside Linkages

Described herein are internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino ($-CH_2-N(CH_3)-O-CH_2-$), thiodiester ($-O-C(O)-S-$), thionocarbamate ($-O-C(O)(NH)-S-$); siloxane ($-O-Si(H)_2-O-$); and N,N'-dimethylhydrazine ($-CH_2-N(CH_3)-N(CH_3)-$). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

In certain embodiments, a phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage.

Certain Motifs

In certain embodiments, oligomeric compounds are gapmers. In such embodiments, oligomeric compounds comprise a central gap region flanked by a 3' wing region and a 5' wing region.

Certain Wings

In certain embodiments oligomeric compounds comprise a 5' wing and/or a 3' wing. In such embodiments, the features of the 3' wing and the features of the 5' wing are selected independently. Thus, in such embodiments, the number of nucleosides in the 5' wing and the number of nucleosides (length) in the 3' wing may be the same or may be different; the modifications, if any, in the 5' wing may be the same as the modifications, if any, in the 3' wing or such modifications, if any, may be different; and the internucleoside linkages in the 5' wing and the internucleoside linkages in the 3' wing may be the same or they may be different.

In certain embodiments a wing comprises one, two, three, four, or five nucleosides (i.e. has a length of 1, 2, 3, 4, or 5). In certain embodiments, the nucleosides of a wing are modified. In certain such embodiments, the nucleosides of the wing are modified to increase affinity of the antisense compound for its target nucleic acid. In certain embodiments, the nucleosides of a wing are nucleosides or nucleotides. In certain such embodiments, the nucleosides or nucleotides of the wing comprise a 2' modification. In certain such embodiments, the nucleosides (nucleosides or nucleotides) of the wing are BNA's. In certain such embodiments, the nucleosides of the wing are selected from α-L-Methyleneoxy (4'-$CH_2$—O-2') BNA, β-D-Methyleneoxy (4'-$CH_2$—O-2') BNA, Ethyleneoxy (4'-$(CH_2)_2$—O-2') BNA, Aminooxy (4'-$CH_2$—O—N(R)-2') BNA and Oxyamino (4'-$CH_2$—N(R)—O-2') BNA. In certain embodiments, the nucleosides of a wing comprise a substituent at the 2' position selected from allyl, amino, azido, thio, O-allyl, O—$C_1$-$C_{10}$ alkyl, —$OCF_3$, O—$(CH_2)_2$—O—$CH_3$, 2'-O$(CH_2)_2$S$CH_3$, O—$(CH_2)_2$—O—N($R_m$)($R_n$), and O—$CH_2$—C(=O)—N($R_m$)($R_n$), where each $R_m$ and $R_n$ is, independently, H or substituted or unsubstituted $C_1$-$C_{10}$ alkyl. In certain embodiments, the nucleosides of a wing are 2'MOE nucleotides.

In certain embodiments, the internucleoside linkages in a wing are naturally occurring internucleoside linkages. In certain embodiments, the internucleoside linkages in a wing are non-naturally occurring internucleoside or internucleoside linkages. In certain such embodiments, the internucleoside linkages in the wing are more resistant to one or more nucleases than naturally occurring internucleoside linkages. In certain such embodiments, the internucleoside linkages in the wing are phosphorothioate linkages (P=S). In certain embodiments where a wing has more than one internucleoside linkage, the internucleoside linkages are the same as one another. In certain embodiments where a wing has more than one internucleoside linkage, the internucleoside linkages are different from each other.

One of ordinary skill in the art will recognize that the features and modifications discussed above may be used in any combination to prepare a wing. The table below provides non-limiting examples showing how one might prepare a wing by selecting a certain number of nucleosides, nucleoside modifications (if any), and internucleoside linkages both within the wing.

| Length | Nucleoside type/ modifications | internucleoside linkages within wing |
|---|---|---|
| 1 | 2' MOE | None |
| 1 | BNA | None |
| 1 | ENA | None |
| 1 | ENA | None |
| 2 | 2' MOE | P=S |
| 2 | BNA | P=S |
| 2 | ENA | P=S |
| 2 | ENA | P=S |
| 2 | 2' MOE | P=O |
| 2 | BNA | P=O |
| 2 | ENA | P=O |
| 2 | ENA | P=O |
| 3 | 2' MOE | P=S |
| 3 | BNA | P=S |
| 3 | ENA | P=S |
| 3 | ENA | P=S |

In certain embodiments in which a wing comprises two, three, four, or five nucleosides, those two, three, four, or five nucleosides those nucleosides are each selected independently. Thus, in certain embodiments in which a wing comprises two, three, four, or five nucleosides, those two, three, four, or five nucleosides all comprise the same modifications, if any. In certain embodiments in which a wing comprises two, three, four, or five nucleosides, one or more of those two, three, four, or five nucleobases comprises one or more modifications that is different from one or more of the modifications of one or more of the remaining nucleosides.

In certain embodiments, one or more nucleoside of a 5' wing is different from at least one other nucleoside of the 5' wing.

In certain embodiments, one or more nucleoside of a 3' wing is different from at least one other nucleoside of the 3' wing.

In certain embodiments, one or more nucleoside of a 5' wing is different from at least one nucleoside of a 3' wing.

In certain embodiments, all of the nucleosides of a 5' wing is different from all of the nucleosides of a 3' wing.

In certain embodiments, one or more internucleoside linkage of a 5' wing is different from at least one other internucleoside linkage of the 5' wing.

In certain embodiments, one or more internucleoside linkage of a 3' wing is different from at least one other internucleoside linkage of the 3' wing.

In certain embodiments, one or more internucleoside linkage of a 5' wing is different from at least one internucleoside linkage of the 3' wing.

In certain embodiments, all of the internucleoside linkages of a 5' wing is different from all of the internucleoside linkages of the 3' wing.

Certain Mixed Wings

In certain embodiments, the invention provides gapmer compounds wherein at least one nucleoside of one wing is differently modified compared to at least one other nucleoside of the same wing. Such oligomeric compounds are referred to as mixed wing oligomeric compounds. In certain embodiments, the modifications (or no modification) of one or more nucleosides of the 3' wing are different from those of one or more other nucleosides of the 3' wing. Such oligomeric compounds may be referred to as 3' mixed wing gapmers. In certain embodiments, the modifications (or no modification) of one or more nucleosides of the 5' wing are different from those of one or more other nucleosides of the 5' wing. Such oligomeric compounds may be referred to as 5' mixed wing gapmers. In certain embodiments, the modifications (or no modification) of one or more nucleosides of the 3' wing are different from those of one or more other nucleosides of the 3' wing and the modifications (or no modification) of one or more nucleosides of the 5' wing are different from those of one or more other nucleosides of the 5' wing. Such oligomeric compounds may be referred to as 3', 5' mixed wing gapmers. In such embodiment, the modifications and combination of modifications at the 3' wing and at the 5' end may be the same or they may be different.

In certain embodiments, mixed wing compounds have desirable properties. Certain nucleoside modifications confer on the oligomeric compound a desirable property, for example increased affinity for a target or nuclease resistance, but also confer an undesirable property, for example increased toxicity. Incorporation of certain other nucleoside modifications results in oligomeric compounds with different profiles of properties. In certain embodiments, one may combine modifications in one or both wings to optimize desirable characteristics and/or minimize undesirable characteristics. In certain embodiments, the wings of a mixed wing oligomeric compound comprise one or more nucleoside comprising a first modification that increases affinity of the oligomeric compound for a target nucleic acid compared to an oligomeric compound comprising unmodified nucleosides; and one or more nucleoside comprising a second modification that results in reduced toxicity compared to an oligomeric compound with wings comprising nucleosides that all comprise the first modification.

In certain embodiments, an oligomeric compound comprises at least one wing comprising at least one MOE substituted nucleoside and at least one LNA. In certain such embodiments, the at least one MOE substituted nucleoside and the at least one LNA are in the 3' wing. In certain such embodiments, the at least one MOE substituted nucleoside and the at least one LNA are in the 5' wing.

One of ordinary skill in the art will recognize that the features and modifications discussed above may be used in any combination to prepare mixed wings. The table below provides non-limiting examples showing how one might prepare mixed wing oligonucleotides by selecting a certain number of nucleosides, nucleoside modifications (if any), and internucleoside linkages within each wing and across wings.

| 5' wing | | | 3' wing | | |
|---|---|---|---|---|---|
| Nucleoside position (5' to 3') | Nucleoside type/ modifications | linkages within wing | Nucleoside position (5' to 3') | Nucleoside type/ modifications | linkages within wing |
| 1 | MOE | P=S | 1 | LNA | P=S |
| 2 | BNA | | 2 | LNA | |
| 1 | LNA | None | 1 | ENA | P=S |
| | | | 2 | DNA | |

-continued

| 5' wing | | | 3' wing | | |
|---|---|---|---|---|---|
| Nucleoside position (5' to 3') | Nucleoside type/ modifications | linkages within wing | Nucleoside position (5' to 3') | Nucleoside type/ modifications | linkages within wing |
| 1 | ENA | P=O | 1 | MOE | None |
| 2 | MOE | | | | |
| 1 | ENA | None | 1 | MOE | P=S |
| | | | 2 | LNA | |
| 1 | MOE | P=S | 1 | MOE | P=S |
| 2 | LNA | | 2 | LNA | |
| 1 | MOE | P=S | 1 | LNA | P=O |
| 2 | LNA | | 2 | MOE | |
| 1 | 2'-F | P=S | 1 | Oxyamino BNA | None |
| 2 | Oxyamino BNA | | | | |
| 1 | ENA | P=S | 1 | ENA | P=S; P=O |
| 2 | ENA | | 2 | ENA | |
| | | | 3 | MOE | |
| 1 | LNA | P=S; P=S | 1 | LNA | P=S; P=S |
| 2 | MOE | | 2 | MOE | |
| 3 | LNA | | 3 | LNA | |
| 1 | MOE | P=S | 1 | LNA | P=S |
| 2 | LNA | | 2 | MOE | |

Certain Asymetric Wings

In certain embodiments, oligomeric compounds comprise asymetric wings. In such embodiments, each of the nucleoside(s) of the 3' wing comprise the same modification (or no modification) and each of the nucleoside(s) of the 5' wing comprise the same modification (or no modification), but the modifications of the 5' wing and the 3' wing are different from one another.

Certain Gaps

In certain embodiments, oligomeric compounds comprise a gap between the 5' wing and the 3' wing. In certain embodiments the gap comprises five, six, seven, eight, nine, ten, eleven, twelve, thirteen, or fourteen nucleosides. In certain embodiments, the nucleosides of the gap are unmodified deoxyribonucleotides. In certain embodiments, the nucleosides of the gap are unmodified ribonucleotides. In certain embodiments, gap modifications (if any) gap result in an antisense compound that, when bound to its target nucleic acid, supports cleavage by an RNase, including, but not limited to, RNase H.

In certain embodiments, the internucleoside linkages in the gap are naturally occurring internucleoside linkages. In certain embodiments, the internucleoside linkages in the gap are non-naturally occurring linkages. In certain such embodiments, the internucleoside linkages in the gap are more resistant to one or more nuclease than naturally occurring internucleoside linkages. In certain such embodiments, the internucleoside linkages in the gap are phosphorothioate linkages (P=S). In certain embodiments, the internucleoside linkages in the gap are all the same as one another. In certain embodiments, the internucleoside linkages within the gap are not all the same.

In certain embodiments, the gap comprises at least 2 nucleosides. In certain embodiments, the gap comprises at least 3 nucleosides. In certain embodiments, the gap comprises at least 4 nucleosides. In certain embodiments, the gap comprises at least 5 nucleosides. In certain embodiments, the gap comprises at least 6 nucleosides. In certain embodiments, the gap comprises at least 7 nucleosides. In certain embodiments, the gap comprises at least 8 nucleosides. In certain embodiments, the gap comprises at least 9 nucleosides. In certain embodiments, the gap comprises at least 10 nucleosides. In certain embodiments, the gap comprises at least 11 nucleosides. In certain embodiments, the gap comprises at least 12 nucleosides. In certain embodiments, the gap comprises at least 13 nucleosides. In certain embodiments, the gap comprises at least 14 nucleosides. In certain embodiments, the gap comprises at least 15 nucleosides. In certain embodiments, the gap comprises at least 16 nucleosides. In certain embodiments, the gap comprises at least 17 nucleosides. In certain embodiments, the gap comprises at least 18 nucleosides. In certain embodiments, the gap comprises at least 19 nucleosides. In certain embodiments, the gap comprises at least 20 nucleosides. In certain embodiments, the gap comprises at least 22 nucleosides. In certain embodiments, the gap comprises at least 23 nucleosides. In certain embodiments, the gap comprises at least 24 nucleosides. In certain embodiments, the gap comprises at least 25 nucleosides. In certain embodiments, the gap comprises at least 26 nucleosides.

One of ordinary skill in the art will recognize that the features and modifications discussed above may be used in any combination to prepare a gap. The table below provides non-limiting examples showing how one might prepare a gap by selecting a certain number of nucleosides, nucleoside modifications (if any), and internucleoside linkages within the gap region.

| Length | Nucleoside type/ modifications | internucleoside linkages within gap |
|---|---|---|
| 5 | DNA | P=S |
| 6 | DNA | P=S |
| 7 | DNA | P=S |
| 8 | DNA | P=S |
| 9 | DNA | P=S |
| 10 | DNA | P=S |
| 11 | DNA | P=S |
| 12 | DNA | P=S |
| 13 | DNA | P=S |
| 14 | DNA | P=S |
| 9 | DNA | P=O |
| 10 | DNA | P=O |
| 11 | DNA | P=O |
| 12 | DNA | P=O |

-continued

| Length | Nucleoside type/ modifications | internucleoside linkages within gap |
|---|---|---|
| 13 | DNA | P=O |
| 14 | DNA | P=O |
| 16 | DNA | P=O |
| 8 | RNA | P=S |
| 9 | RNA | P=S |
| 10 | RNA | P=S |
| 11 | RNA | P=S |
| 12 | RNA | P=S |

Certain Gapped Oligomeric Compounds

One of ordinary skill in the art will recognize that the wings and the gaps discussed above may be selected and then combined in a variety of combinations to generate gapped oligomeric compounds, including, but not limited to, gapped antisense oligomeric compounds, and gapped antisense oligonucleotides. The features (length, modifications, linkages) of the 5' wing and the 3' wing may be selected independently of one another. The features of the gap include at least one difference in modification compared to the features of the 5' wing and at least one difference compared to the features of the 3' wing (i.e., there must be at least one difference in modification between neighboring regions to distinguish those neighboring regions from one another). The features of the gap may otherwise be selected independently.

In certain embodiments, the linkages within a wing and the internucleoside linkages within the gap are the same. In certain embodiments, the internucleoside linkages within a wing and the internucleoside linkages within the gap are different. In certain such embodiments, the internucleoside linkage bridging the wing and the gap are the same as the monomeric linkages in the wing. In certain embodiments, the internucleoside linkage bridging the wing and the gap are the same as the internucleoside linkages in the gap. In certain embodiments, oligomeric compounds have uniform linkages throughout the compound. In certain such embodiments, all of the linkages are phosphorothioate (P=S) linkages.

One of ordinary skill in the art will recognize that the 3' wings, 5' wings, gaps, and linkages discussed above may be used in any combination to prepare a gapmer. The table below provides non-limiting examples showing how one might prepare a gapmer by independently selecting features for a 5' wing, a gap, a 3' wing and linkages bridging the gap and each wing.

In certain embodiments, the present invention provides oligomeric compounds of any of a variety of ranges of lengths. In certain embodiments, the invention provides oligomeric compounds comprising oligonucleotides consisting of X to Y linked nucleosides, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds comprising oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 1 to 14, 1 to 15, 11 to 16, 1 to 17, 1 to 18, 11 to 19, 11 to 20, 11 to 21, 11 to 22, 11 to 23, 1 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25

| 5' Wing | | 5' Bridge | Gap | | | 3' Bridge | 3' Wing | | |
|---|---|---|---|---|---|---|---|---|---|
| Length | Nucleoside | Link | Link | Length | Nucleoside | Link | Link | Length | Nucleoside | Link |
| 2 | MOE | P=S | P=S | 6 | DNA | P=S | P=S | 2 | MOE | P=S |
| 2 | BNA | P=S | P=O | 8 | DNA | P=O | P=S | 3 | BNA | P=S |
| 1 | MOE | None | P=S | 10 | DNA | P=S | P=S | 1 | MOE | P=S |
| 2 | MOE | P=S | P=S | 8 | RNA | P=S | P=S | 2 | MOE | P=S |
| 3 | ENA | P=S | P=S | 8 | RNA | P=S | P=S | 3 | MOE | P=S |
| 3 | DNA | P=O | P=O | 10 | RNA | P=S | P=O | 3 | 2'OH | P=O |
| 2 | 2-F | P=S | P=S | 5 | RNA | P=S | P=S | 2 | 2'-F | P=S |
| 1 | MOE | P=O | P=S | 16 | DNA | P=O | P=S | 4 | MOE | P=S |

In certain embodiments, oligomeric compounds may be designed by combining, for example, the previous table exemplifying certain sets of mixed wings with any gap.

to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

In certain embodiments, oligomeric compounds are mixed wing gapmers. In certain such embodiments, one or both wings of oligomeric compounds comprise one or more non-bicyclic 2' substituted nucleoside and one or more BNA nucleoside. Such motifs include, but are not limited to:

2' mod-BNA-(DNA)$_{4-20}$-BNA;
2' mod-BNA-(DNA)$_{4-20}$-2' mod;
BNA-2' mod-(DNA)$_{4-20}$-BNA;
BNA-2' mod-(DNA)$_{4-20}$-2' mod;
BNA-(DNA)$_{4-20}$-2' mod-BNA;
BNA-(DNA)$_{4-20}$-BNA-2'-mod;
2' mod-BNA-(DNA)$_{4-20}$-BNA-2' mod;
2' mod-BNA-(DNA)$_{4-20}$-2' mod-BNA;
2' mod-BNA-(DNA)$_{4-20}$-BNA-BNA;
2' mod-BNA-(DNA)$_{4-20}$-2' mod-2' mod;
BNA-2' mod-(DNA)$_{4-20}$-BNA-2' mod;
BNA-2' mod-(DNA)$_{4-20}$-2' mod-BNA;
BNA-2' mod-(DNA)$_{4-20}$-BNA-BNA;
BNA-2' mod-(DNA)$_{4-20}$-2' mod-2' mod;
2' mod-2' mod-(DNA)$_{4-20}$-2' mod-BNA;
2' mod-2' mod-(DNA)$_{4-20}$-BNA-2' mod;
2' mod-2' mod-BNA-(DNA)$_{4-20}$-BNA-2' mod;
2' mod-2' mod-BNA-(DNA)$_{4-20}$-2' mod-BNA;
2' mod-2' mod-BNA-(DNA)$_{4-20}$-BNA-BNA;
2' mod-2' mod-BNA-(DNA)$_{4-20}$-2' mod-2' mod;
2' mod-BNA-2' mod-(DNA)$_{4-20}$-BNA-2' mod;
2' mod-BNA-2' mod-(DNA)$_{4-20}$-2' mod-BNA;
2' mod-BNA-2' mod-(DNA)$_{4-20}$-BNA-BNA;
2' mod-BNA-2' mod-(DNA)$_{4-20}$-2' mod-2' mod;
2' mod-2' mod-2' mod-(DNA)$_{4-20}$-2' mod-BNA;
2' mod-2' mod-2' mod-(DNA)$_{4-20}$-BNA-2' mod;
2' mod-2' mod-BNA-(DNA)$_{4-20}$-2' mod-BNA-2' mod;
2' mod-2' mod-BNA-(DNA)$_{4-20}$-2' mod-2' mod-BNA;
2' mod-2' mod-BNA-(DNA)$_{4-20}$-2' mod-BNA-BNA;
2' mod-2' mod-BNA-(DNA)$_{4-20}$-2' mod-2' mod-2' mod;
2' mod-BNA-2' mod-(DNA)$_{4-20}$-2' mod-BNA-2' mod;
2' mod-BNA-2' mod-(DNA)$_{4-20}$-2' mod-2' mod-BNA;
2' mod-BNA-2' mod-(DNA)$_{4-20}$-2' mod-BNA-BNA;
2' mod-BNA-2' mod-(DNA)$_{4-20}$-2' mod-2' mod-2' mod;
2' mod-2' mod-2' mod-(DNA)$_{4-20}$-2' mod-2' mod-BNA; and
2' mod-2' mod-2' mod-(DNA)$_{4-20}$-2' mod-BNA-2' mod;

wherein "2' mod" is any non-bicyclic modified nucleoside comprising a substituent at the 2' position and "BNA" is any bicyclic nucleic acid. In certain embodiments, the 2' mod is selected from MOE, 2'-F, 2'-alkyl, and 2'-O-alkyl and the BNA is selected from α-L-LNA, β-D-LNA, ENA, Oxyamino BNA (2'-O—N(CH$_3$)—CH$_2$-4') and Aminooxy BNA (2'-N(CH$_3$)—O—CH$_2$-4'). In embodiments comprising two or more 2' mod nucleosides each of those two or more 2' mod nucleosides is selected independently and thus may be the same or different from one another. In embodiments comprising two or more BNA nucleosides each of those two or more BNA nucleosides is selected independently and thus may be the same or different from one another. In certain embodiments, each "2' mod" on the above list represents a MOE and each "BNA" on the above list represents an LNA.

Certain nucleosides, such as certain BNA nucleosides, confer increased potency and/or activity on an oligomeric compound relative to other nucleosides, such as MOE, but also confer increased toxicity. In certain embodiments, oligomeric compounds comprising mixed wings have better potency than oligomeric compounds with uniform MOE wings and less toxicity than uniform BNA compounds. In certain of such embodiments, mixed wing oligomeric compounds have higher therapeutic indexes than either oligomeric compounds comprising uniform BNA wings or oligomeric compound comprising uniform MOE wings. In certain such embodiments, the BNA is selected from α-L-LNA, β-D-LNA, ENA, Oxyamino BNA (2'-O—N(CH$_3$)—CH$_2$-4') and Aminooxy BNA (2'-N(CH$_3$)—O—CH$_2$-4'). In certain embodiments, such oligomeric compounds comprise mixed backbones. In certain embodiments, such oligomeric compounds comprises uniform backbones. In certain embodiments at least one internucleoside linkage is a phosphorothioate. In certain embodiments each internucleoside linkage is a phosphorothioate.

Conjugate Groups

In certain embodiments, oligomeric compounds are modified by covalent attachment of one or more conjugate groups. In general, conjugate groups modify one or more properties of the attached oligomeric compound including but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

Certain conjugate groups amenable to the present invention include lipid moieties such as a cholesterol moiety (Letsinger et al., Proc. Natl. Acad. Sci. USA, 1989, 86, 6553); cholic acid (Manoharan et al., Bioorg. Med. Chem. Lett., 1994, 4, 1053); a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765); a thiocholesterol (Oberhauser et al., Nucl. Acids Res., 1992, 20, 533); an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49); a phospholipid, e.g., di-hexadecyl-rac-glycerol or triethyl-ammonium-1,2-di-O-hexadecyl-rac-glycero-3-H-phosphonate (Manoharan et al., Tetrahedron Lett., 1995, 36, 3651; Shea et al., Nucl. Acids Res., 1990, 18, 3777); a polyamine or a polyethylene glycol chain (Manoharan et al., Nucleosides & Nucleotides, 1995, 14, 969); adamantane acetic acid (Manoharan et al., Tetrahedron Lett., 1995, 36, 3651); a palmityl moiety (Mishra et al., Biochim. Biophys. Acta, 1995, 1264, 229); or an octadecylamine or hexylamino-carbonyl-oxycholesterol moiety (Crooke et al., J. Pharmacol. Exp. Ther., 1996, 277, 923).

Linking groups or bifunctional linking moieties such as those known in the art are amenable to the compounds provided herein. Linking groups are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Antisense Mechanisms

In certain embodiments, the invention provides oligomeric compounds that are antisense compounds. Antisense mechanisms are all those involving the hybridization of a compound with target nucleic acid, wherein the outcome or effect of the hybridization is either target degradation or target occupancy with concomitant stalling of the cellular machinery involving, for example, transcription or splicing.

In certain embodiment, compounds of the invention exert a biological effect through RNase H, which is a cellular endonuclease that cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of DNA-like oligonucleotide-mediated inhibition of gene expression. It is known that gapmers are capable of eliciting RNase H cleavage provided the gap is DNA-like and at least 4 nucleotides in length.

Antisense mechanisms rely on hybridization of the antisense oligomeric compound to the target nucleic acid. Accordingly, in certain embodiments, the invention provides oligomeric compounds that are complementary to a target nucleic acid.

As used herein, "targeting" or "targeted to" refer to the process of designing an oligomeric compound such that the compound specifically hybridizes with a selected nucleic acid molecule.

"Targeting" an oligomeric compound to a particular target nucleic acid molecule can be a multistep process. The process usually begins with the identification of a target nucleic acid whose expression is to be modulated. As used herein, the terms "target nucleic acid" and "nucleic acid encoding a target gene" encompass DNA encoding a selected target gene, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent.

One of skill in the art will be able to design, synthesize, and screen oligomeric compounds of different nucleobase sequences to identify a sequence that results in antisense activity. For example, one may design an oligomeric compound that inhibits expression of a target protein. Methods for designing, synthesizing and screening oligomeric compounds for antisense activity against a preselected target nucleic acid can be found, for example in and "Antisense Drug Technology, Principles, Strategies, and Applications" Edited by Stanley T. Crooke, CRC Press, Boca Raton, Fla., which is incorporated by reference in its entirety for any purpose.

Complementarity

One skilled in the art recognizes that the inclusion of mismatches is possible without eliminating the activity of the antisense compound. Therefore, described herein are antisense compounds that may contain up to about 20% nucleotides that disrupt base pairing of the antisense compound to the target. Preferably the compounds contain no more than about 15%, more preferably not more than about 10%, most preferably not more than about 5% or no mismatches. The remaining nucleotides do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid. Percent complementarity of an oligonucleotide is calculated by dividing the number of complementary nucleobases by the total number of nucleobases of the oligonucleotide. Percent complementarity of a region of an oligonucleotide is calculated by dividing the number of complementary nucleobases in the region by the total number of nucleobases region.

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of ordinary skill in the art is capable of determining an appropriate number of mismatches between oligonucleotides, or between an oligonucleotide and a target nucleic acid, such as by determining melting temperature ($T_m$). $T_m$ or $\Delta T_m$ can be calculated by techniques that are familiar to one of ordinary skill in the art. For example, techniques described in Freier et al. (*Nucleic Acids Research*, 1997, 25, 22: 4429-4443) allow one of ordinary skill in the art to evaluate nucleotide modifications for their ability to increase the melting temperature of an RNA:DNA duplex.

Identity

Antisense compounds, or a portion thereof, may have a defined percent identity to a SEQ ID NO, or a compound having a specific Isis number. As used herein, a sequence is identical to the sequence disclosed herein if it has the same nucleobase pairing ability. For example, a RNA which contains uracil in place of thymidine in the disclosed sequences of the compounds described herein would be considered identical as they both pair with adenine. This identity may be over the entire length of the oligomeric compound, or in a portion of the antisense compound (e.g., nucleobases 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compounds taught herein, or non-identical versions of the antisense compounds taught herein are also provided herein. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. In the context of the instant description, the complement of an active target segment may constitute a single portion. In preferred embodiments, the oligonucleotides provided herein are at least 80%, at least 85%, at least 90%, at least 95%, at least 96%, at least 97%, at least 98%, at least 99% or 100% identical to at least a portion of the complement of the active target segments presented herein. Percent identity of an oligonucleotide is calculated by dividing the number of identical nucleobases by the total number of nucleobases of the oligonucleotide. Percent identity of a region of an oligonucleotide is calculated by dividing the number of identity nucleobases in the region by the total number of nucleobases region.

Oligomer Synthesis

In certain embodiments, provided herein are compounds having reactive phosphorus groups useful for forming internucleoside linkages including for example phosphodiester and phosphorothioate internucleoside linkages. Methods of preparation and/or purification of precursors or antisense compounds are not a limitation of the compositions or methods provided herein. Methods for synthesis and purification of DNA, RNA, and the antisense compounds are well known to those skilled in the art.

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds provided herein can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

Salts, Prodrugs and Bioequivalents

The antisense compounds provided herein comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleobases that are cleaved (e.g., by incorporating phosphodiester backbone linkages at the ends) to produce the active compound.

The term "pharmaceutically acceptable salts" refers to physiologically and pharmaceutically acceptable salts of the compounds described herein: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided.

Formulations

The antisense compounds provided herein may also be admixed, encapsulated, conjugated or otherwise associated with other molecules, molecule structures or mixtures of compounds.

Also described herein are pharmaceutical compositions and formulations which include the antisense compounds provided herein. The pharmaceutical compositions may be administered in a number of ways depending upon whether local or systemic treatment is desired and upon the area to be treated. In a preferred embodiment, administration is topical to the surface of the respiratory tract, particularly pulmonary, e.g., by nebulization, inhalation, or insufflation of powders or aerosols, by mouth and/or nose.

The pharmaceutical formulations described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). In a preferred embodiment, the pharmaceutical formulations are prepared for pulmonary administration in an appropriate solvent, e.g., water or normal saline, possibly in a sterile formulation, with carriers or other agents to allow for the formation of droplets of the desired diameter for delivery using inhalers, nasal delivery devices, nebulizers, and other devices for pulmonary delivery. Alternatively, the pharmaceutical formulations may be formulated as dry powders for use in dry powder inhalers.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Combinations

Compositions provided herein can contain two or more antisense compounds. In another related embodiment, compositions can contain one or more antisense compounds, particularly oligonucleotides, targeted to a first nucleic acid and one or more additional antisense compounds targeted to a second nucleic acid target. Alternatively, compositions can contain two or more antisense compounds targeted to different regions of the same nucleic acid target. Two or more combined compounds may be used together or sequentially. Compositions can also be combined with other non-antisense compound therapeutic agents.

Kits, Research Reagents and Diagnostics

The antisense compounds provided herein can be utilized for diagnostics, and as research reagents and kits. Furthermore, antisense compounds, which are able to inhibit gene expression or modulate gene expression with specificity, are often used by those of ordinary skill to elucidate the function of particular genes or to distinguish between functions of various members of a biological pathway.

For use in kits and diagnostics, the antisense compounds described herein, either alone or in combination with other compounds or therapeutics, can be used as tools in differential and/or combinatorial analyses to elucidate expression patterns of a portion or the entire complement of genes expressed within cells and tissues. Methods of gene expression analysis are well known to those skilled in the art.

Therapeutics

Antisense compounds provided herein can be used to modulate the expression of a target gene in an animal, such as a human. The provided compounds also can be used to treat metabolic disorders or modulate one or more disease indications. In one non-limiting embodiment, the methods comprise the step of administering to said animal in need of therapy for a disease or condition associated with a target gene an effective amount of an antisense compound that modulates expression of the target gene. Antisense compounds provided herein which effectively modulate expression of a target RNA or protein products of expression are considered active antisense compounds. Active antisense compounds also include compounds which effectively modulate one or more of a number of disease indications, including metabolic and cardiovascular disease indications, examples of which are described below.

Modulation of expression of a target gene can be measured in a bodily fluid, which may or may not contain cells; tissue; or organ of the animal. Methods of obtaining samples for analysis, such as body fluids (e.g., sputum, serum, urine), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers, or disease indications, associated with the target gene expression in the aforementioned fluids, tissues or organs, collected from an animal contacted with one or more compounds described herein, by routine clinical methods known in the art. These biomarkers include but are not limited to: liver transaminases, bilirubin, albumin, blood urea nitrogen, creatine and other markers of kidney and liver function; interleukins, tumor necrosis factors, intracellular adhesion molecules, C-reactive protein, chemokines, cytokines, and other markers of inflammation.

Methods of obtaining serum or plasma samples for analysis and methods of preparation of the serum samples to allow for analysis are well known to those skilled in the art. With regard to measurements of lipoproteins, cholesterol, triglyceride and cholesteryl esters, the terms "serum" and "plasma" are herein used interchangeably.

The antisense compounds provided herein can be utilized in pharmaceutical compositions by adding an effective amount of a compound to a suitable pharmaceutically acceptable diluent or carrier. Acceptable carriers and diluents are well known to those skilled in the art. Selection of a diluent or carrier is based on a number of factors, including, but not limited to, the solubility of the compound and the route of administration. Such considerations are well understood by those skilled in the art. In one aspect, the antisense compounds described herein inhibit expression of a target gene. The compounds can also be used in the manufacture of a medicament for the treatment of diseases and disorders related to a target gene.

Methods whereby bodily fluids, organs or tissues are contacted with an effective amount of one or more of the antisense compounds or compositions provided herein are also contemplated. Bodily fluids, organs or tissues can be contacted with one or more of the compounds resulting in modulation of target gene expression in the cells of bodily fluids, organs or tissues. An effective amount can be determined by monitoring the modulatory effect of the antisense compound or compounds or compositions on target nucleic acids or their products by methods routine to the skilled artisan.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

EXAMPLES

General

The sequences listed in the examples have been annotated to indicate the location and type of nucleoside modifications and conjugate groups. All of the nucleosides that are not annotated are β-D-deoxyribonucleosides. Each modified nucleoside is preceded by a subscripted letter or a letter followed by a number wherein the letter indicates the type of modification and the number indicates a further modification at a particular position. In particular, subscript "m" indicates a 2'-O-methyl group; subscript "l" indicates a bicyclic nucleoside having a 4'-$CH_2$—O-2' bridge, also referred to as LNA; subscript "g" indicates a bicyclic nucleoside having a 4'-$(CH_2)_2$—O-2' bridge, also referred to as ENA; subscript "#1" (# is 5 or 6) indicates a bicyclic nucleoside having a 4'-$CH_2$—O-2' bridge (LNA) having a further substituent group located at the 5' or 6' position of the bicyclic nucleoside which can also be chiral (R) or (S); subscript "e" indicates 2'-O-methoxyethyl (MOE) group; subscript "a" indicates a 2'-O—N-methylacetamido group (2'-O—CH$_2$C(=O)NHCH$_3$); superscript "me" preceding a cytosine residue indicates a 5-methyl cytosine; and C$_{16}$ indicates a C$_{16}$ conjugate group attached to the 5'-terminus of the oligomeric compound via a diamide linkage (5'-OCH$_2$C(=O)N(H)(CH$_2$)$_4$N(H)C(=O)—(CH$_2$)$_{14}$CH$_3$). For example U$_e$ is a modified uridine having a 2'-O-methoxyethyl group and U$_{51}$ is an LNA modified uridine having a further substituent at the 5'-position. The sequence listing accompanying this filing provides certain nucleic acid sequences independent of chemical modification. Though that listing identifies each sequence as either "RNA" or "DNA" as required, those sequences may be modified with any combination of chemical modifications and/or motifs.

Example 1

Cell Culture and Treatment with Oligomeric Compounds

The effect of oligomeric compounds on target nucleic acid expression can be tested in any one of a number of cultured or primary cell lines. Cells lines can be obtained from publicly available sources, such as the American Type Culture Collection (Manassas, Va.). Cells are cultured according to methods well known to those of ordinary skill in the art.

When cells reached appropriate confluency, they were treated with oligonucleotide using Lipofectin™ as described. When cells reached 65-75% confluency, they were treated with oligonucleotide. Oligonucleotide was mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 μg/mL per 100 nM oligonucleotide. This transfection mixture was incubated at room temperature for approximately 0.5 hours. For cells grown in 96-well plates, wells were washed once with 100 μL OPTI-MEM™-1 and then treated with 130 μL of the transfection mixture. Cells grown in 24-well plates or other standard tissue culture plates were treated similarly, using appropriate volumes of medium and oligonucleotide. Cells were treated and data were obtained in duplicate or triplicate. After approximately 4-7 hours of treatment at 37° C., the medium containing the transfection mixture was replaced with fresh culture medium. Cells were harvested 16-24 hours after oligonucleotide treatment.

Control oligonucleotides are used to determine the optimal oligomeric compound concentration for a particular cell line. Furthermore, when oligomeric compounds are tested in oligomeric compound screening experiments or phenotypic assays, control oligonucleotides are tested in parallel.

The concentration of oligonucleotide used varies from cell line to cell line. To determine the optimal oligonucleotide concentration for a particular cell line, the cells are treated with a positive control oligonucleotide at a range of concentrations. The concentration of positive control oligonucleotide that results in 80% inhibition of the target mRNA is then utilized as the screening concentration for new oligonucleotides in subsequent experiments for that cell line. If 80% inhibition is not achieved, the lowest concentration of positive control oligonucleotide that results in 60% inhibition of the target mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM when the antisense oligonucleotide is transfected using a liposome reagent 1 μM to 40 μM when the antisense oligonucleotide is transfected by electroporation.

Example 2

Real-Time Quantitative PCR Analysis of Target mRNA Levels

Quantitation of target mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the target gene being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 μL PCR cocktail (2.5×PCR buffer minus MgCl$_2$, 6.6 mM MgCl$_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 μL of RiboGreen™ working reagent (RiboGreen™ reagent diluted 1:350 in 10 mM Tris-HCl, 1 mM EDTA, pH 7.5) was pipetted into a 96-well plate containing 30 μL purified cellular RNA. The plate was read in a CytoFluor 4000 (PE Applied Biosystems) with excitation at 485 nm and emission at 530 nm.

The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

Probes and primers for use in real-time PCR were designed to hybridize to target-specific sequences. Primer and probe sequences and target genes to which they hybridize are presented in Table 1. The target-specific PCR probes have FAM covalently linked to the 5' end and TAMRA or MGB covalently linked to the 3' end, where FAM is the fluorescent dye and TAMRA or MGB is the quencher dye.

TABLE 1

Target-specific primers and probes for use in real-time PCR

| Target Name | Species | Sequence Description | Sequence (5' to 3') | SEQ ID NO |
|---|---|---|---|---|
| PTEN | Mouse | Forward Primer | GCCACAGGCTCCCAGACAT | 1 |
| PTEN | Mouse | Reverse Primer | TCCATCCTCTTGATATCTCCTTTTG | 2 |
| PTEN | Mouse | Probe | ACAGCCATCATCAAAGAGATCGTTAGCAGAA | 3 |
| PTEN | Mouse | Forward Primer | ATGACAATCATGTTGCAGCAATTC | 4 |
| PTEN | Mouse | Reverse Primer | CGATGCAATAAATATGCACAAATCA | 5 |
| PTEN | Mouse | Probe | CTGTAAAGCTGGAAAGGGACGGACTGGT | 6 |

Example 3

Short LNA-Modified 2-10-2 Gapmer Antisense Compounds with Varying Numbers of 2'-MOE Wing Modifications Targeting PTEN.

The studies described herein were performed using a number of modified short antisense oligonucleotides to determine whether nucleotide modification could mitigate hepatatoxicity associated with the locked nucleic acid (LNA) moiety. The sequences and motifs of antisense compounds used in these studies are shown in Table 2. Each compound is targeted to published PTEN sequences including Genbank Accession No. U92437.1 (SEQ ID NO: 7), (site 140). Each compound is a 2-10-2 gapmer (shortmer), which is 14 nucleotides in length having a central "gap" region consisting often 2'-deoxynucleotides that is flanked by a 5' and a 3' "wing" region, each 2 nucleotides in length. As shown in Table 2, wing nucleotides of the individual ASO compounds bear distinct sugar modifications.

TABLE 2

Short LNA Antisense Compounds with MOE modifications

| ISIS # | Sequence | SEQ ID NO |
|---|---|---|
| 394424 | $T_e{}^{me}C_e$ATGGCTGCAG$^{me}C_eT_e$ | 8 |
| 392056 | $T_l{}^{me}C_l$ATGGCTGCAG$^{me}C_lT_l$ | 8 |
| 396570 | $T_e{}^{me}C_e$ATGGCTGCAG$^{me}C_lT_l$ | 8 |
| 396571 | $T_l{}^{me}C_e$ATGGCTGCAG$^{me}C_lT_l$ | 8 |
| 396574 | $T_e{}^{me}C_e$ATGGCTGCAG$^{me}C_lT_l$ | 8 |
| 396572 | $T_l{}^{me}C_l$ATGGCTGCAG$^{me}C_eT_l$ | 8 |
| 396573 | $T_l{}^{me}C_l$ATGGCTGCAG$^{me}C_lT_e$ | 8 |
| 396575 | $T_l{}^{me}C_l$ATGGCTGCAG$^{me}C_eT_e$ | 8 |

Male 6-week old Balb/c mice (Jackson Laboratory, Bar Harbor, Me.) were given a single 8 μmol/kg intraperitoneal injection of a PTEN antisense oligonucleotide (ASO) from Table 3. Mice were sacrificed 72 hours following ASO or control (saline) injection and serum concentrations of liver transaminases (alanine aminotransferase [ALT] and aspartate aminotransferase [AST]) measured in international units (IU)/L as indicators of liver damage, using methods well-known by those of ordinary skill in the art. Target (PTEN) mRNA levels in the liver were determined by methods well-known by those of ordinary skill in the art, and reduction in target mRNA listed as percent of untreated control (% UTC).

The results from one such study, using LNA-modified 2-10-2 gapmers having varying numbers of 2'-MOE wing modifications are summarized in Table 3.

TABLE 3

Liver Transaminases and Target mRNA Reduction Following Administration of LNA-Modified and 2'-MOE modified Antisense Oligonucleotides

| ISIS # | ALT | AST | PTEN mRNA (% UTC) | Wing Chemistry |
|---|---|---|---|---|
| saline | 39 | 68 | 100.0 | N/A |
| 394424 | 38 | 75 | 89.7 | 2'-MOE wings |
| 392056 | 1249 | 770 | 32.4 | LNA wings |
| 396570 | 51 | 84 | 57.8 | LNA wings w/a 2' MOE at 5' pos 1 |
| 396571 | 42 | 79 | 63.8 | LNA wings w/a 2' MOE at 5' pos 2 |
| 396574 | 36 | 67 | 71.0 | 2'-MOE at 5' wing LNA at 3' wing |
| 396572 | 497 | 327 | 48.8 | LNA wings w/a 2'-MOE at 3' pos. 13 |
| 396573 | 531 | 316 | 46.7 | LNA wings w/a 2'-MOE at 3' pos. 14 |
| 396575 | 473 | 341 | 41.8 | LNA at 5' wing 2'-MOE at 3' wing |

Administration of 2-10-2 gapmer antisense oligonucleotides with 2'-MOE nucleotide wings (ISIS 394424) had ALT/AST levels which are commensurate with levels described in the art associated with other 2'MOE gapmer antisense olignucleotides. In contrast, the gapmer antisense oligonucleotide with LNA-modified wings (ISIS 392056) reduced target (PTEN) mRNA, but resulted in severely elevated levels of liver transaminases in serum of treated mice, indicating hepatotoxicity. The gapmer antisense oligonucleotides having 2'-MOE nucleotides added to either of the 3' and the 5' wing regions resulted in a mitigation of the elevated serum transaminases caused by the LNA gapmer, ISIS 392056. Gapmers with 2'-MOE modification of only the 5' wings (one or both nucleotides) of LNA-modified antisense oligonucleotides (ISIS 396570, ISIS 396571 and ISIS 396574) resulted in serum transaminase concentrations near that of the 2'MOE gapmer antisense oligonucleotide (ISIS 394424) following administration to mice, indicating that substitution of specific LNA nucleoside(s) with 2'-modified nucleoside(s) provided a compound with an improved hepatotoxicity profile. These compounds also reduced target PTEN mRNA relative to the UTC. 2'-MOE modification of 3' wing nucleotides (ISIS 396572, ISIS 396573, ISIS 396575) resulted in a mitigation of the transaminase elevation caused by the LNA gapmer antisense oligonucleotide. Together, these data indicate that 2'-MOE modification of wing nucleotides can mitigate hepatatoxicity of 2-10-2 LNA gapmers to levels which are commensurate with other 2'-MOE gapmers, while maintaining target mRNA reduction.

Example 4

Short 2-10-2 Gapmer Antisense Compounds with C16 Conjugates on Terminal 5' Nucleotide Targeting ApoB.

The studies described herein were performed using two modified 2-10-2 gapmer antisense oligonucleotides to determine whether nucleotide modification could mitigate hepatatoxicity associated with the locked nucleic acid (LNA) moiety. The sequences and motifs of antisense compounds are shown in Table 4. Each compound is targeted to published ApoB sequences including Genbank Accession No. U92437.1 (SEQ ID NO: 7), (site 140). Each compound is a 2-10-2 gapmer (shortmer), which is 14 nucleotides in length having a central "gap" region consisting often 2'-deoxynucleotides that is flanked by a 5' and a 3' "wing" region, each 2 nucleotides in length. As shown in Table 4, wing nucleotides of the individual ASO compounds bear distinct sugar modifications. Each compound included a 5' terminal C16-G having the following structure:

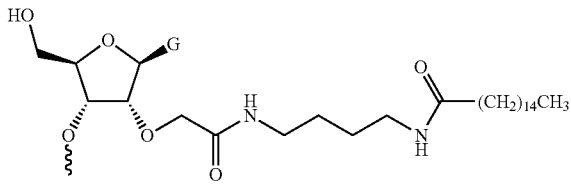

TABLE 4

Short Antisense Compounds with wing modifications

| ISIS # | Sequence | SEQ ID NO |
|---|---|---|
| 391871 | $C_{16}$-$GG_e$TACATGGAAGT$_e C_e$ | 9 |
| 391872 | $C_{16}$-$GG_l$TACATGGAAGT$_l C_l$ | 9 |

Male 6-week old Balb/c mice (Jackson Laboratory, Bar Harbor, Me.) were administered twice per week for three weeks a single dose of a ApoB antisense oligonucleotide (ASO) from Table 5 by intraperitoneal injection at a concentration of 2.5, 1.0, 0.4 or 0.16 µmol/kg. Mice were sacrificed 48 hours following last administration of ASO or control (saline) injection and serum concentrations of liver transaminases (alanine aminotransferase [ALT] and aspartate aminotransferase [AST]) measured in international units (IU)/L, and bilirubin, free cholesterol, triglycerides, HDL and LDL, measured in international units mg/L. These endpoints were measured using methods well-known by those of ordinary skill in the art. Results are presented in Table 5.

Target (ApoB) mRNA levels in the liver were determined by methods well-known by those of ordinary skill in the art, and reduction in target mRNA listed as percent of untreated control (% UTC). As illustrated in Table 5, ApoB mRNA levels were reduced in a dose-dependent manner.

TABLE 5

Target mRNA Reduction Following Administration of LNA-Modified and 2'-MOE modified Antisense Oligonucleotides

| ISIS # | Dose (µmol/kg) | ApoB mRNA (% UTC) | Wing Chemistry |
|---|---|---|---|
| saline | | 100.0 | N/A |
| 391871 | 0.16 | 105 | 2'-MOE wings w/$C_{16}$ at 5' pos. 1 |
| | 0.4 | 95 | |
| | 1.0 | 82 | |
| | 2.5 | 51 | |
| 391872 | 0.16 | 98 | LNA wings w/$C_{16}$ at 5' pos. 1 |
| | 0.4 | 50 | |
| | 1.0 | 8 | |
| | 2.5 | 0.8 | |

Plasma concentrations of total cholesterol, free cholesterol, triglycerides, transaminases, bilirubin, LDL and HDL were measured according to routine experimental procedures. The results are summarized in Table 6 below.

TABLE 6

Liver Transaminases, Bilirubin levels, Cholesterol levels, Triglycerides levels, HDL and LDL levels Following Administration of LNA-Modified and 2'-MOE modified Antisense Oligonucleotides

| ISIS # | Dose | ALT | AST | Bilirubin | Cholesterol | HDL | Triglycerides | LDL |
|---|---|---|---|---|---|---|---|---|
| 391871 | 0.16 | 38 | 95 | 0.175 | 106 | 78 | 253 | 8.0 |
| | 0.4 | 40 | 98 | 0.150 | 109 | 79 | 256 | 8.0 |
| | 1 | 32 | 44 | 0.175 | 108 | 82 | 219 | 6.8 |
| | 2.5 | 38 | 133 | 0.150 | 90 | 65 | 236 | 5.5 |
| 391872 | 0.16 | 31 | 55 | 0.175 | 101 | 78 | 212 | 6.8 |
| | 0.4 | 30 | 78 | 0.150 | 77 | 58 | 220 | 4.3 |
| | 1 | 38 | 100 | 0.175 | 28 | 19 | 109 | 2.0 |
| | 2.5 | 38 | 59 | 0.200 | 14 | 6 | 76 | 0.0 |

At the end of the study, liver, kidney and spleen were harvested from animals treated with the oligomeric compounds and were weighed to assess gross organ alterations. Approximate average tissue weights for each short antisense compounds are presented in Table 7.

TABLE 7

Effects of LNA-Modified and 2'-MOE modified Antisense Oligonucleotides Targeted to ApoB on Tissue Weight in Balb/c mice.

| ISIS # | Dose (μmol/kg) | liver weight | spleen weight |
| --- | --- | --- | --- |
| saline | N/A | 1.00 | 1.00 |
| 391871 | 0.16 | 0.92 (−8%) | 0.97 (−3%) |
|  | 0.4 | 0.98 (−2%) | 1.02 (+2%) |
|  | 1.0 | 0.97 (−3%) | 0.99 (−1%) |
|  | 2.5 | 1.08 (+8%) | 1.12 (+12%) |
| 391872 | 0.16 | 0.92 (−8%) | 1.04 (+3%) |
|  | 0.4 | 0.98 (−2%) | 1.18 (+18%) |
|  | 1.0 | 1.10 (+10%) | 1.01 (+1%) |
|  | 2.5 | 1.10 (+10%) | 1.11 (+11%) |

Example 5

Short 2-14-2 Gapmer Antisense Compounds with Various Substitutions on 2'-O Position Targeting PTEN.

The studies described herein were performed using modified antisense oligonucleotides to determine whether nucleotide modification could mitigate hepatatoxicity associated with the locked nucleic acid (LNA) moiety. The sequences and motifs of antisense compounds used in these studies are shown in Table 8. Stereochemistry for certain compounds is described in Table 9. For example, 5'-(S)-Me-LNA indicates an S configuration at the 5 carbon atom for 5-CH$_3$-LNA. Each compound is targeted to published PTEN sequences including Genbank Accession No. U92437.1 (SEQ ID NO: 7), (site 140). Each compound is a 2-14-2 gapmer, which is 18 nucleotides in length having a central "gap" region consisting of fourteen 2'-deoxynucleotides that is flanked by a 5' and a 3' "wing" region, each 2 nucleotides in length. As shown in Table 8, wing nucleotides of the individual ASO compounds bear distinct sugar modifications.

TABLE 8

Short LNA Antisense Compounds with MOE modifications

| ISIS # | Sequence | SEQ ID NO |
| --- | --- | --- |
| 394420 | $^{me}C_eT_e$GCTAGCCTCTGGATT$_eT_e$ | 10 |
| 394425 | $^{me}C_lT_l$GCTAGCCTCTGGATT$_lT_l$ | 10 |
| 399700 | $^{me}C_eT_l$GCTAGCCTCTGGATT$_lT_l$ | 10 |
| 399701 | $^{me}C_lT_e$GCTAGCCTCTGGATT$_lT_l$ | 10 |
| 399702 | $^{me}C_eT_e$GCTAGCCTCTGGATT$_lT_l$ | 10 |
| 399703 | $^{me}C_lT_l$GCTAGCCTCTGGATT$_eT_e$ | 10 |
| 400521 | $C_{51}U_{51}$GCTAGCCTCTGGATU$_{51}U_{51}$ | 10 |
| 400522 | $C_{61}U_{61}$GCTAGCCTCTGGATU$_{61}U_{61}$ | 10 |
| 400523 | $C_{61}U_{61}$GCTAGCCTCTGGATU$_{61}U_{61}$ | 10 |
| 400524 | $C_{61}U_{61}$GCTAGCCTCTGGATU$_{61}U_{61}$ | 10 |
| 400525 | $C_{61}U_{61}$GCTAGCCTCTGGATU$_{61}U_{61}$ | 10 |

Male 6-week old Balb/c mice (Jackson Laboratory, Bar Harbor, Me.) were given a single 10 or 2 μmol/kg intraperitoneal injection of a PTEN antisense oligonucleotide (ASO) from Table 9. Mice were sacrificed 72 hours following ASO or control (saline) injection and serum concentrations of liver transaminases (alanine aminotransferase [ALT] and aspartate aminotransferase [AST]) measured in international units (IU)/L as indicators of liver damage, using methods well-known by those of ordinary skill in the art. Target (PTEN) mRNA levels in the liver were determined by methods well-known by those of ordinary skill in the art, and reduction in target mRNA listed as percent of untreated control (% UTC). The results are summarized in Table 9.

TABLE 9

Liver Transaminases and Target mRNA Reduction Following Administration of LNA-Modified and 2'-MOE modified Antisense Oligonucleotides

| ISIS # | Dose (μmol/kg) | ALT | AST | PTEN mRNA (% UTC) | Wing Chemistry |
| --- | --- | --- | --- | --- | --- |
| saline |  | 39 | 66 | 100 | N/A |
| 394420 | 2 | 30 | 78 | 79 | 2'-MOE wings |
|  | 10 | 49 | 91 | 26 |  |
| 394425 | 2 | 41 | 78 | 11 | LNA wings |
|  | 10 | 2453 | 2240 | 2 |  |
| 399700 | 2 | 45 | 148 | 36 | LNA wings w/a |
|  | 10 | 71 | 245 | 6 | 2'-MOE at 5' pos. 1 |
| 399701 | 2 | 42 | 140 | 48 | LNA wings w/a |
|  | 10 | 40 | 109 | 10 | 2'-MOE at 5' pos. 2 |
| 399702 | 2 | 36 | 78 | 69 | 2'-MOE at 5' wing |
|  | 10 | 41 | 99 | 19 | LNA at 3' wing |
| 399703 | 2 | 33 | 99 | 17 | LNA at 5' wing |
|  | 10 | 807 | 731 | 2 | 2'-MOE at 3' wing |
| 400521 | 2 | 37 | 81 | 21 | $_{51}$ = 5'-(S)—Me—BNA |
|  | 10 | 152 | 182 | 4 | wings |

TABLE 9-continued

Liver Transaminases and Target mRNA Reduction Following Administration of LNA-Modified and 2'-MOE modified Antisense Oligonucleotides

| ISIS # | Dose (µmol/kg) | ALT | AST | PTEN mRNA (% UTC) | Wing Chemistry |
|---|---|---|---|---|---|
| 400522 | 2 | 44 | 113 | 18 | $_{61}$ = 6'-(R)—Me—BNA wings |
|  | 10 | 794 | 696 | 4 |  |
| 400523 | 2 | 43 | 153 | 17 | $_{61}$ = 6'-(S)—Me—BNA wings |
|  | 10 | 1374 | 818 | 4 |  |
| 400524 | 2 | 31 | 59 | 23 | $_{61}$ = 6'-(R)—CH$_2$OCH$_3$—BNA wings |
|  | 10 | 269 | 263 | 4 |  |
| 400525 | 2 | 43 | 110 | 21 | $_{61}$ = 6'-(S)—CH$_2$OCH$_3$—BNA wings |
|  | 10 | 765 | 636 | 3 |  |

*pos. = position in nucleotide sequence

Administration of 2-14-2 gapmer antisense oligonucleotides with 2'-MOE nucleotide wings (ISIS 394420) had ALT/AST levels which are commensurate with levels described in the art associated with other 2'MOE gapmer antisense olignucleotides. In contrast, the gapmer antisense oligonucleotide with LNA-modified wings (ISIS 394425) reduced target (PTEN) mRNA, but resulted in elevated levels of liver transaminases in serum of treated mice, indicating hepatotoxicity. The gapmer antisense oligonucleotides having 2'-MOE nucleotides added to either of the 3' and the 5' wing regions resulted in a mitigation of the elevated serum transaminases caused by the LNA gapmer, ISIS 394425. Gapmers with 2'-MOE modification of only the 5' wings (one or both nucleotides) of LNA-modified antisense oligonucleotides (ISIS 399700, ISIS 399701 and ISIS 399702) resulted in serum transaminase concentrations near that of the 2'MOE gapmer antisense oligonucleotide (ISIS 394420) following administration to mice, indicating that substitution of specific LNA nucleoside(s) with 2'-modified nucleoside(s) provided a compound with an improved hepatotoxicity profile. These compounds also reduced target PTEN mRNA relative to the UTC. Gapmers with 2'-MOE modification of 3' wing (both nucleotides) (ISIS 399703) resulted in a mitigation of the transaminase elevation caused by the LNA gapmer antisense oligonucleotide. Together, these data indicate that 2'-MOE modification of wing nucleotides can mitigate hepatatoxicity of 2-14-2 LNA gapmers to levels which are commensurate with other 2'-MOE gapmers, while maintaining target mRNA reduction.

Example 6

Short 1-9-2 Gapmer Short Antisense Compounds with various substitutions on 2'-O position Targeting PTEN.

The studies described herein were performed using a number of modified 1-9-2 gapmer oligonucleotides to determine whether nucleotide modification could mitigate hepatatoxicity associated with the locked nucleic acid (LNA) moiety. The sequences and motifs of antisense compounds used in these studies are shown in Table 11. Each compound is targeted to published PTEN sequences including Genbank Accession No. U92437.1 (SEQ ID NO: 7), (site 140). Each compound is a 1-9-2 gapmer (shortmer), which is 12 nucleotides in length having a central "gap" region consisting of nine 2'-deoxynucleotides that is flanked by a 5' and a 3' "wing" region. The 5' wing region contains one nucleotide in length and the 3' wing region contains two nucleotides in length. As shown in Table 11, wing nucleotides of the individual ASO compounds bear distinct sugar modifications.

TABLE 11

Short LNA Antisense Compounds with MOE modifications

| ISIS # | Sequence | SEQ ID NO |
|---|---|---|
| 396151 | T$_e$GGTCCAGAG$^{me}$C$_e$$^{me}$C$_e$ | 11 |
| 396153 | T$_l$GGTCCAGAG$^{me}$C$_l$$^{me}$C$_l$ | 11 |
| 401350 | T$_e$GGTCCAGAG$^{me}$C$_l$$^{me}$C$_l$ | 11 |
| 401349 | T$_l$GGTCCAGAG$^{me}$C$_e$$^{me}$C$_e$ | 11 |
| 401351 | T$_d$GGTCCAGAG$^{me}$C$_l$$^{me}$C$_l$ | 11 |
| 401352 | C$_{16}$-TGGTCCAGAG$^{me}$C$_l$$^{me}$C$_l$ | 11 |

Male 6-week old Balb/c mice (Jackson Laboratory, Bar Harbor, Me.) were given a single 10 or 3.2, 1, or 0.32 µmol/kg intraperitoneal injection of a PTEN antisense oligonucleotide (ASO) from Table 11. Mice were sacrificed 72 hours following ASO or control (saline) injection and serum concentrations of liver transaminases (alanine aminotransferase [ALT] and aspartate aminotransferase [AST]) measured in international units (IU)/L as indicators of liver damage, using methods well-known by those of ordinary skill in the art. Target (PTEN) mRNA levels in the liver were determined by methods well-known by those of ordinary skill in the art, and reduction in target mRNA listed as percent of untreated control (% UTC). Results are summarized in Table 12.

TABLE 12

Liver Transaminases and Target mRNA Reduction Following Administration of LNA-Modified and 2'-MOE modified Antisense Oligonucleotides

| ISIS # | Dose (µmol/kg) | ALT | AST | PTEN mRNA (% UTC) | Wing Chemistry |
|---|---|---|---|---|---|
| saline | N/A | 39 | 66 | 100 | N/A |
| 396151 | 0.32 | 53 | 69 | 97 | 2'-MOE wings |
|  | 1 | 53 | 98 | 82 |  |
|  | 3.2 | 64 | 97 | 71 |  |
|  | 10 | 89 | 101 | 23 |  |
| 396153 | 0.32 | 52 | 120 | 63 | LNA wings |
|  | 1 | 71 | 110 | 24 |  |
|  | 3.2 | 750 | 467 | 8 |  |
|  | 10 | 9681 | 4233 | 11 |  |

TABLE 12-continued

Liver Transaminases and Target mRNA Reduction Following Administration of LNA-Modified and 2'-MOE modified Antisense Oligonucleotides

| ISIS # | Dose (μmol/kg) | ALT | AST | PTEN mRNA (% UTC) | Wing Chemistry |
|---|---|---|---|---|---|
| 401350 | 0.32 | 55 | 105 | 80 | 2'-MOE at 5' wing |
| | 1 | 61 | 125 | 49 | LNA at 3' wing |
| | 3.2 | 69 | 107 | 15 | |
| | 10 | 2183 | 1033 | 6 | |
| 401349 | 0.32 | 67 | 188 | 74 | LNA at 5' wing |
| | 1 | 69 | 125 | 48 | 2'-MOE at 3' wing |
| | 3.2 | 118 | 357 | 12 | |
| | 10 | 1323 | 645 | 6 | |
| 401351 | 0.32 | 39 | 52 | 91 | 2'-NMA at 5' wing |
| | 1 | 51 | 53 | 50 | LNA at 3' wing |
| | 3.2 | 79 | 165 | 16 | |
| | 10 | 4446 | 2025 | 6 | |
| 401352 | 0.32 | 39 | 53 | 55 | C16 at 5' pos. 1 |
| | 1 | 64 | 112 | 14 | LNA at 3' wing |
| | 3.2 | 3571 | 1385 | 6 | |
| | 10 | 7831 | 4687 | 2 | |

The invention claimed is:

1. A gapmer oligonucleotide consisting of 12 to 24 linked nucleosides wherein the gapmer oligonucleotide consists of three regions:
- a gap region consisting of 6 to 10 linked deoxynucleosides;
- a 5' wing region positioned at the 5' end of the gap region and consisting of 1 to 7 linked nucleosides, wherein each nucleoside of the 5' wing region comprises a modified sugar, wherein at least one nucleoside of the 5' wing region is a 2'-O(CH$_2$)$_2$OCH$_3$ modified nucleoside or a 2'-O—CH$_3$ modified nucleoside; and
- a 3' wing region positioned at the 3' end of the gap region and consisting of 1 to 7 linked nucleosides, wherein each nucleoside of the 3' wing region comprises a modified sugar, wherein at least one nucleoside of the 3' wing region is a methyleneoxy (4'-CH$_2$—O-2') bicyclic nucleoside or an ethyleneoxy (4'-CH$_2$CH$_2$—O-2')

bicyclic nucleoside; and wherein the gapmer oligonucleotide has a plurality of phosphorothioate internucleoside linkages.

2. The gapmer oligonucleotide of claim 1, wherein at least one nucleoside of the 5' wing region is a 2'-O(CH$_2$)$_2$OCH$_3$ modified nucleoside.

3. The gapmer oligonucleotide of claim 1, wherein at least one nucleoside of the 5' wing region is a 2'-OCH$_3$ modified nucleoside.

4. The gapmer oligonucleotide of claim 1, wherein at least one nucleoside of the 3' wing is an ethyleneoxy (4'-CH$_2$CH$_2$—O-2') bicyclic nucleoside.

5. The gapmer oligonucleotide of claim 4, wherein at least one nucleoside of the 5' wing is a 2'-O(CH$_2$)$_2$OCH$_3$ modified nucleoside.

6. The gapmer oligonucleotide of claim 1, wherein at least one nucleoside of the 3' wing is a methyleneoxy (4'-CH$_2$—O-2') bicyclic nucleoside.

7. The gapmer oligonucleotide of claim 1, wherein the wing regions each consist of 1 to 3 linked nucleosides.

8. The gapmer oligonucleotide of claim 4, wherein at least one nucleoside of the 5' wing is a 2'-O—CH$_3$ modified nucleoside.

9. The gapmer oligonucleotide of claim 1, wherein the 3' wing comprises at least one non-bicyclic 2'-modified nucleoside.

10. The gapmer oligonucleotide of claim 1, wherein the 5' wing comprises at least one 4' to 2' bicyclic nucleoside.

11. The gapmer oligonucleotide of claim 1, wherein each internucleoside linkage of the gapmer oligonucleotide is a phosphorothioate internucleoside linkage.

12. The gapmer oligonucleotide of claim 1, wherein the gapmer oligonucleotide consists of 15 to 20 linked nucleosides.

13. The gapmer oligonucleotide of claim 1, wherein the 5' wing region consists of 1 to 5 linked nucleosides.

14. The gapmer oligonucleotide of claim 1, wherein the 3' wing region consists of 1 to 5 linked nucleosides.

15. The gapmer oligonucleotide of claim 1, wherein the gap region consists of 8 to 10 linked deoxynucleosides.

16. A conjugate comprising the gapmer oligonucleotide of claim 1 and a conjugate group.

17. The conjugate of claim 16, wherein the conjugate group comprises a palmityl group.

18. The conjugate of claim 16, wherein the conjugate group comprises a linking group.

19. The gapmer oligonucleotide of claim 6, wherein at least one nucleoside of the 5' wing is a 2'-O(CH$_2$)$_2$OCH$_3$ modified nucleoside.

20. The gapmer oligonucleotide of claim 6, wherein at least one nucleoside of the 5' wing is a 2'-O—CH$_3$ modified nucleoside.

21. The gapmer oligonucleotide of claim 10, wherein at least one nucleoside of the 5' wing is a methyleneoxy (4'-CH$_2$—O-2') bicyclic nucleoside.

22. The gapmer oligonucleotide of claim 10, wherein at least one nucleoside of the 5' wing is an ethyleneoxy (4'-CH$_2$CH$_2$—O-2') bicyclic nucleoside.

23. The gapmer oligonucleotide of claim 5, wherein the wing regions each consist of 1 to 5 linked nucleosides.

24. The gapmer oligonucleotide of claim 5, wherein the wing regions each consist of 1 to 3 linked nucleosides.

25. The gapmer oligonucleotide of claim 8, wherein the wing regions each consist of 1 to 5 linked nucleosides.

26. The gapmer oligonucleotide of claim 8, wherein the wing regions each consist of 1 to 3 linked nucleosides.

27. The gapmer oligonucleotide of claim 19, wherein the wing regions each consist of 1 to 5 linked nucleosides.

28. The gapmer oligonucleotide of claim 19, wherein the wing regions each consist of 1 to 3 linked nucleosides.

29. The gapmer oligonucleotide of claim 20, wherein the wing regions each consist of 1 to 5 linked nucleosides.

30. The gapmer oligonucleotide of claim 20, wherein the wing regions each consist of 1 to 3 linked nucleosides.

31. A pharmaceutical composition comprising the gapmer oligonucleotide of claim 1 and a pharmaceutically acceptable diluent or carrier.

\* \* \* \* \*